United States Patent
Chong et al.

(10) Patent No.: US 9,039,653 B2
(45) Date of Patent: May 26, 2015

(54) RETENTION SYSTEMS AND METHODS

(75) Inventors: Colin A. Chong, Burbank, CA (US);
Eric M. Lorenzen, Granada Hills, CA (US); Rafael Bikovsky, Oak Park, CA (US); Arsen Ibranyan, Glendale, CA (US); Matthew William Yavorsky, Los Angeles, CA (US); Mona-Lisa Alexander, San Marino, CA (US); R. Paul Mounce, Burbank, CA (US); Paul F. Bente, IV, South Pasadena, CA (US)

(73) Assignee: MEDTRONIC MINIMED, INC., Northridge, CA (US)

(*) Notice: Subject to any disclaimer, the term of this patent is extended or adjusted under 35 U.S.C. 154(b) by 337 days.

(21) Appl. No.: 12/974,117

(22) Filed: Dec. 21, 2010

(65) Prior Publication Data

US 2011/0160650 A1    Jun. 30, 2011

Related U.S. Application Data

(63) Continuation-in-part of application No. 12/649,172, filed on Dec. 29, 2009, and a continuation-in-part of application No. 12/650,378, filed on Dec. 30, 2009, and a continuation-in-part of application No.
(Continued)

(51) Int. Cl.
*A61M 5/14* (2006.01)
*A61M 5/142* (2006.01)
(Continued)

(52) U.S. Cl.
CPC ....... *A61M 5/14248* (2013.01); *Y10T 29/49826* (2015.01); *A61M 5/1413* (2013.01);
(Continued)

(58) Field of Classification Search
CPC ............ A61M 5/1452; A61M 5/1456; A61M 5/14566
USPC ........ 604/93.01, 64, 131, 135, 152, 151, 154, 604/155
See application file for complete search history.

(56) References Cited

U.S. PATENT DOCUMENTS

| | | |
|---|---|---|
| 3,701,345 A | 10/1972 | Heilman et al. |
| 3,994,295 A | 11/1976 | Wulff |

(Continued)

FOREIGN PATENT DOCUMENTS

| | | |
|---|---|---|
| DE | 31 44 825 | 5/1983 |
| EP | 00 927 12 | 11/1983 |

(Continued)

OTHER PUBLICATIONS

Partial Search Report dated Mar. 1, 2011 from related patent application No. PCT/US2010/060892.
(Continued)

*Primary Examiner* — Laura Bouchelle
(74) *Attorney, Agent, or Firm* — Foley & Lardner LLP

(57) ABSTRACT

A system for retaining a fluid delivery device, the fluid delivery device may include a reservoir and a plunger arm operatively connected to a plunger head arranged for movement within the reservoir, the plunger arm having an arm portion operatively engageable with a drive member configured to move the plunger arm and the plunger head when the plunger arm and the plunger head are connected to the drive member. The system may include a rigid member arranged for movement and a bias member configured to urge the rigid member toward the plunger arm to force the plunger arm against the drive member to operatively engage the plunger arm to the drive member.

57 Claims, 19 Drawing Sheets

Related U.S. Application Data

12/649,619, filed on Dec. 30, 2009, now Pat. No. 8,308,679, and a continuation-in-part of application No. 12/650,287, filed on Dec. 30, 2009, now Pat. No. 8,858,500.

(51) Int. Cl.
*A61M 5/145* (2006.01)
*A61M 5/158* (2006.01)
*A61M 5/168* (2006.01)

(52) U.S. Cl.
CPC ............. *A61M5/1456* (2013.01); *A61M 5/158* (2013.01); *A61M 5/1684* (2013.01); *A61M 2005/14252* (2013.01); *A61M 2005/14268* (2013.01); *A61M 2005/1583* (2013.01); *A61M 2005/1585* (2013.01); *A61M 2205/3317* (2013.01); *A61M 2205/332* (2013.01); *A61M 2205/3389* (2013.01); *A61M 2209/045* (2013.01)

(56) References Cited

U.S. PATENT DOCUMENTS

| | | | |
|---|---|---|---|
| 4,633,232 | A | 12/1986 | Nelson et al. |
| 5,122,123 | A | 6/1992 | Vaillancourt |
| 5,176,662 | A | 1/1993 | Bartholomew et al. |
| 5,236,416 | A | 8/1993 | McDaniel et al. |
| 5,334,188 | A | 8/1994 | Inoue et al. |
| 5,533,981 | A * | 7/1996 | Mandro et al. ............... 604/208 |
| 5,628,309 | A | 5/1997 | Brown |
| 5,662,612 | A | 9/1997 | Niehoff |
| 5,954,697 | A | 9/1999 | Srisathapat et al. |
| 6,283,943 | B1 | 9/2001 | Dy et al. |
| 6,299,131 | B1 | 10/2001 | Ryan |
| 6,423,035 | B1 | 7/2002 | Das et al. |
| 6,461,329 | B1 | 10/2002 | Van Antwerp et al. |
| 6,699,218 | B2 | 3/2004 | Flaherty et al. |
| 6,727,689 | B1 | 4/2004 | Furlong et al. |
| 6,740,059 | B2 | 5/2004 | Flaherty |
| 6,749,587 | B2 | 6/2004 | Flaherty |
| 6,945,760 | B2 | 9/2005 | Gray et al. |
| 6,960,192 | B1 | 11/2005 | Flaherty et al. |
| 7,018,360 | B2 | 3/2006 | Flaherty et al. |
| 7,396,353 | B2 * | 7/2008 | Lorenzen et al. .......... 604/891.1 |
| 8,152,771 | B2 | 4/2012 | Mogensen et al. |
| 8,308,679 | B2 | 11/2012 | Hanson et al. |
| 8,435,209 | B2 | 5/2013 | Hanson et al. |
| 2001/0034506 | A1 | 10/2001 | Hirschman et al. |
| 2001/0041869 | A1 | 11/2001 | Causey et al. |
| 2004/0002682 | A1 | 1/2004 | Kovelman et al. |
| 2004/0162521 | A1 | 8/2004 | Bengtsson |
| 2005/0065472 | A1 | 3/2005 | Cindrich et al. |
| 2005/0101932 | A1 | 5/2005 | Cote et al. |
| 2006/0061353 | A1 | 3/2006 | Etherington et al. |
| 2006/0079765 | A1 | 4/2006 | Neer et al. |
| 2006/0200020 | A1 | 9/2006 | Brister et al. |
| 2007/0049865 | A1 | 3/2007 | Radmer et al. |
| 2007/0060871 | A1 | 3/2007 | Istoc et al. |
| 2007/0073236 | A1 | 3/2007 | Mernoe et al. |
| 2007/0191770 | A1 | 8/2007 | Moberg et al. |
| 2007/1917021 | | 8/2007 | Ofer et al. |
| 2007/0270744 | A1 | 11/2007 | Dacquay et al. |
| 2008/0051697 | A1 | 2/2008 | Mounce et al. |
| 2008/0051711 | A1 | 2/2008 | Mounce et al. |
| 2008/0051714 | A1 * | 2/2008 | Moberg et al. ............... 604/135 |
| 2008/0097321 | A1 * | 4/2008 | Mounce et al. ............... 604/132 |
| 2008/0097381 | A1 | 4/2008 | Moberg et al. |
| 2008/0269687 | A1 | 10/2008 | Chong et al. |
| 2008/0281270 | A1 | 11/2008 | Cross et al. |
| 2008/0319414 | A1 | 12/2008 | Yodfat et al. |
| 2009/0069750 | A1 | 3/2009 | Schraga |
| 2009/0156990 | A1 | 6/2009 | Wenger et al. |
| 2009/0182301 | A1 * | 7/2009 | Bassarab et al. ............... 604/416 |
| 2009/0259183 | A1 | 10/2009 | Chong et al. |
| 2009/0259198 | A1 | 10/2009 | Chong et al. |
| 2009/0326458 | A1 | 12/2009 | Chong et al. |
| 2010/0137790 | A1 | 6/2010 | Yodfat |
| 2010/0152658 | A1 | 6/2010 | Hanson et al. |
| 2010/0274180 | A1 | 10/2010 | Donovan et al. |
| 2011/0166512 | A1 | 7/2011 | Both et al. |
| 2011/0178461 | A1 | 7/2011 | Chong et al. |
| 2011/0213306 | A1 | 9/2011 | Hanson et al. |
| 2012/0215163 | A1 | 8/2012 | Hanson et al. |
| 2013/0253422 | A1 | 9/2013 | Hanson et al. |

FOREIGN PATENT DOCUMENTS

| | | |
|---|---|---|
| EP | 0317808 | 5/1989 |
| EP | 0 937 475 | 8/1999 |
| EP | 1177802 | 2/2002 |
| EP | 1 752 172 | 8/2005 |
| EP | 2 077 128 B1 | 12/2010 |
| GB | 2 327 151 | 1/1999 |
| JP | 11-339439 | 12/1999 |
| WO | WO-86/02562 | 5/1986 |
| WO | WO-99/33504 | 7/1999 |
| WO | WO-00/47254 | 8/2000 |
| WO | WO-01/68163 | 9/2001 |
| WO | WO-2006/031500 | 3/2006 |
| WO | WO-2006/076656 | 7/2006 |
| WO | WO-2006/121921 A2 | 11/2006 |
| WO | WO-2006/122406 | 11/2006 |
| WO | WO-2006/124756 | 11/2006 |
| WO | WO-2008/024810 | 2/2008 |
| WO | WO-2008/024812 A2 | 2/2008 |
| WO | WO-2008/024814 A2 | 2/2008 |
| WO | WO-2008/078318 | 7/2008 |
| WO | WO-2008/092782 | 8/2008 |
| WO | WO-2008/133702 | 11/2008 |
| WO | WO-2008/133702 A1 | 11/2008 |
| WO | WO-2009/001346 | 12/2008 |
| WO | WO-2009/016638 | 2/2009 |
| WO | WO-2009/033032 A1 | 3/2009 |
| WO | WO-2009/066288 | 5/2009 |
| WO | WO-2009/093759 A1 | 7/2009 |
| WO | WO-2009/098291 A1 | 8/2009 |
| WO | WO-2009/106517 | 9/2009 |
| WO | WO-2009/125398 A2 | 10/2009 |
| WO | WO-2009/135667 | 11/2009 |
| WO | WO-2009/144726 A1 | 12/2009 |
| WO | WO-2010/042814 | 4/2010 |
| WO | WO-2011/082256 | 7/2011 |
| WO | WO-2011/090629 | 7/2011 |
| WO | WO-2011/119768 | 9/2011 |

OTHER PUBLICATIONS

Partial Search Report dated Mar. 21, 2011 from related patent application No. PCT/US2010/060895.
Partial Search Report dated Mar. 23, 2011 from related patent application No. PCT/US2010/047590.
US Office Action dated Mar. 3, 2011 from related U.S. Appl. No. 12/649,172.
US Office Action dated Oct. 7, 2010 from related U.S. Appl. No. 12/649,172.
Search Report dated Jul. 13, 2011 from related PCT application No. PCT/US2010/060895.
Partial International Search Report from related PCT application No. PCT/US2012/064454, mailed Feb. 4, 2013, 5 pages.
Japanese Office Action from related Japanese Patent Application No. 2012-528022, issued Mar. 25, 2014, 3 pages.
U.S. Office Action from related U.S. Appl. No. 12/553,038, mailed Jun. 20, 2013.
U.S. Office Action from related U.S. Appl. No. 13/103,014, mailed May 22, 2013.
International Search Report and Written Opinion from related PCT application No. PCT/US2012/064454, mailed Jun. 12, 2013.
US Notice of Allowance dated Jul. 7, 2014, from related U.S. Appl. No. 12/650,287.

(56) References Cited

OTHER PUBLICATIONS

US Notice of Allowance dated Jul. 24, 2014, from related U.S. Appl. No. 13/015,028.
US Office Action dated Jul. 1, 2014 from related U.S. Appl. No. 12/974,106.
International Search Report for PCT/US2011/066504, dated Jul. 6, 2012.
English Abstract of DE3144825, 2 pages, 1983.
English Abstract of EP0092712, 1 page, 1983.
English Abstract of EP1752172, 1 page, 2005.
U.S. Office Action dated Sep. 5, 2014, from related U.S. Appl. No. 12/650,378.
U S. Notice of Allowance dated Sep. 22, 2014, from related U.S. Appl. No. 13/015,051.
U.S. Office Action dated Sep. 11, 2014, from related U.S. Appl. No. 13/462,752.
U.S. Office Action dated Sep. 8, 2014, from related U.S. Appl. No. 13/421,564.
U.S. Notice of Allowance dated Oct. 20, 2014, from related patent U.S. Appl. No. 12/974,106.
U.S. Office Action dated Jan. 9, 2015, from related U.S. Appl. No. 12/649,172.
International Search Report and Written Opinion from related PCT application No. PCT/US2011/066501, mailed Dec. 12, 2012, 23 pages.
International Search Report and Written Opinion from related PCT application No. PCT/US2011/066504, mailed Oct. 24, 2012. 29 pages.
International Search Report and Written Opinion from related PCT application No. PCT/US2012/022881, mailed Aug. 28, 2012, 21 pages.
International Search Report and Written Opinion from related PCT application No. PCT/US2012/022883, mailed Aug. 7, 2012, 21 pages.
International Search Report and Written Opinion from related PCT application No. PCT/US2012/055661, mailed Dec. 11, 2012, 11 pages.
U.S. Notice of Allowance from related U.S. Appl. No. 13/235,228, mailed Dec. 20, 2012, 12 pages.
U.S. Non-Final Office Action from related U.S. Appl. No. 12/553,038, mailed Dec. 28, 2012, 10 pages.
International Search Report and Written Opinion from related patent application No. PCT/US2010/062414.
IPRP dated Mar. 6, 2012 from related PCT/US2010/047590 application.

\* cited by examiner

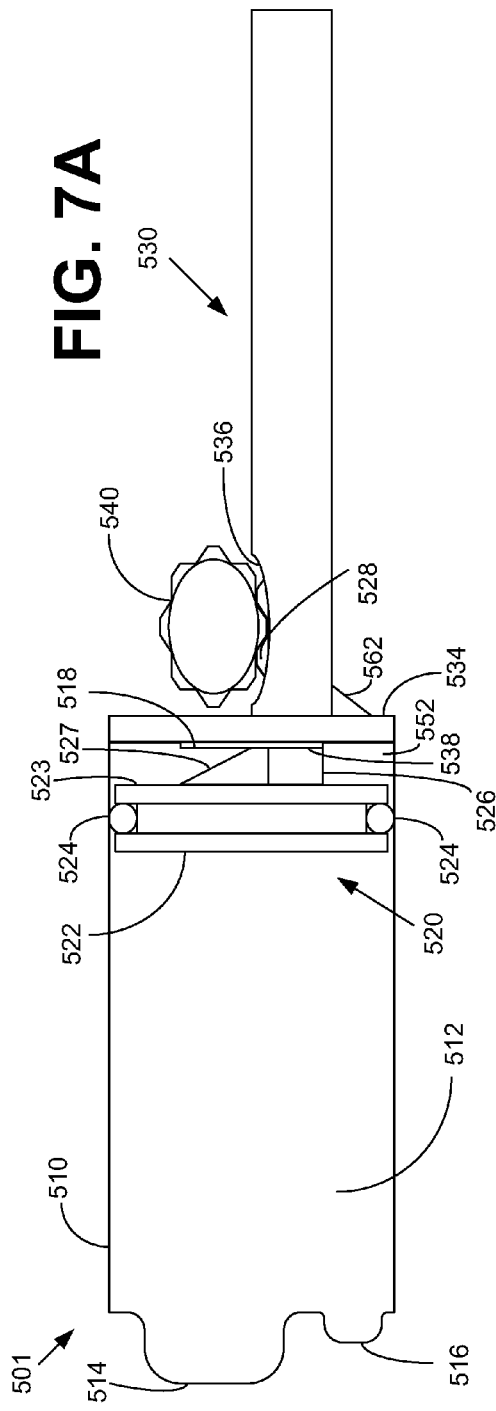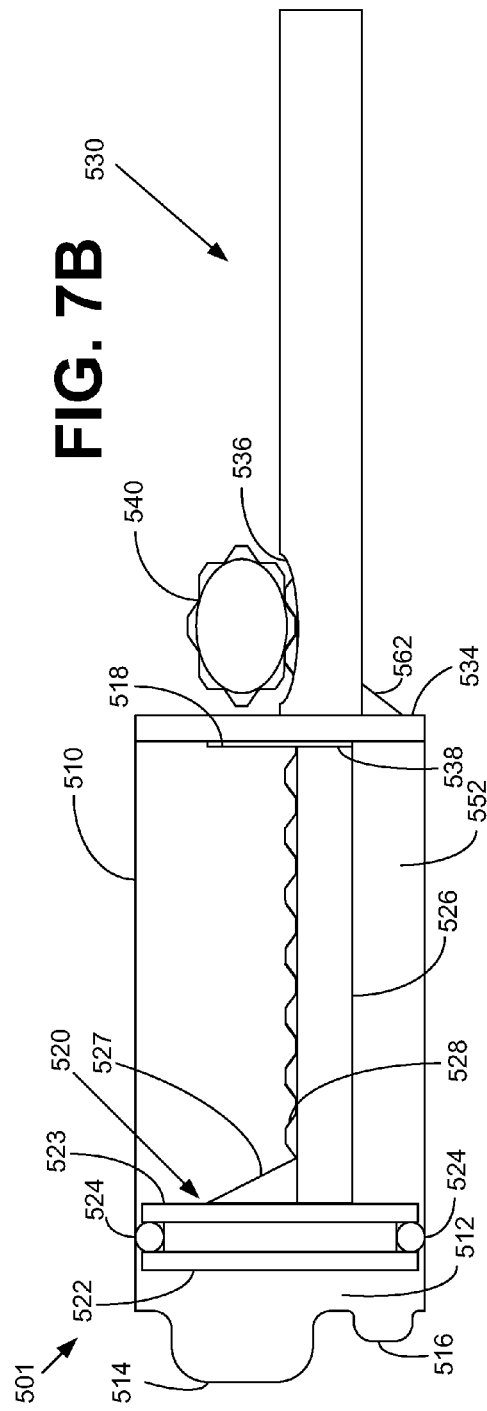

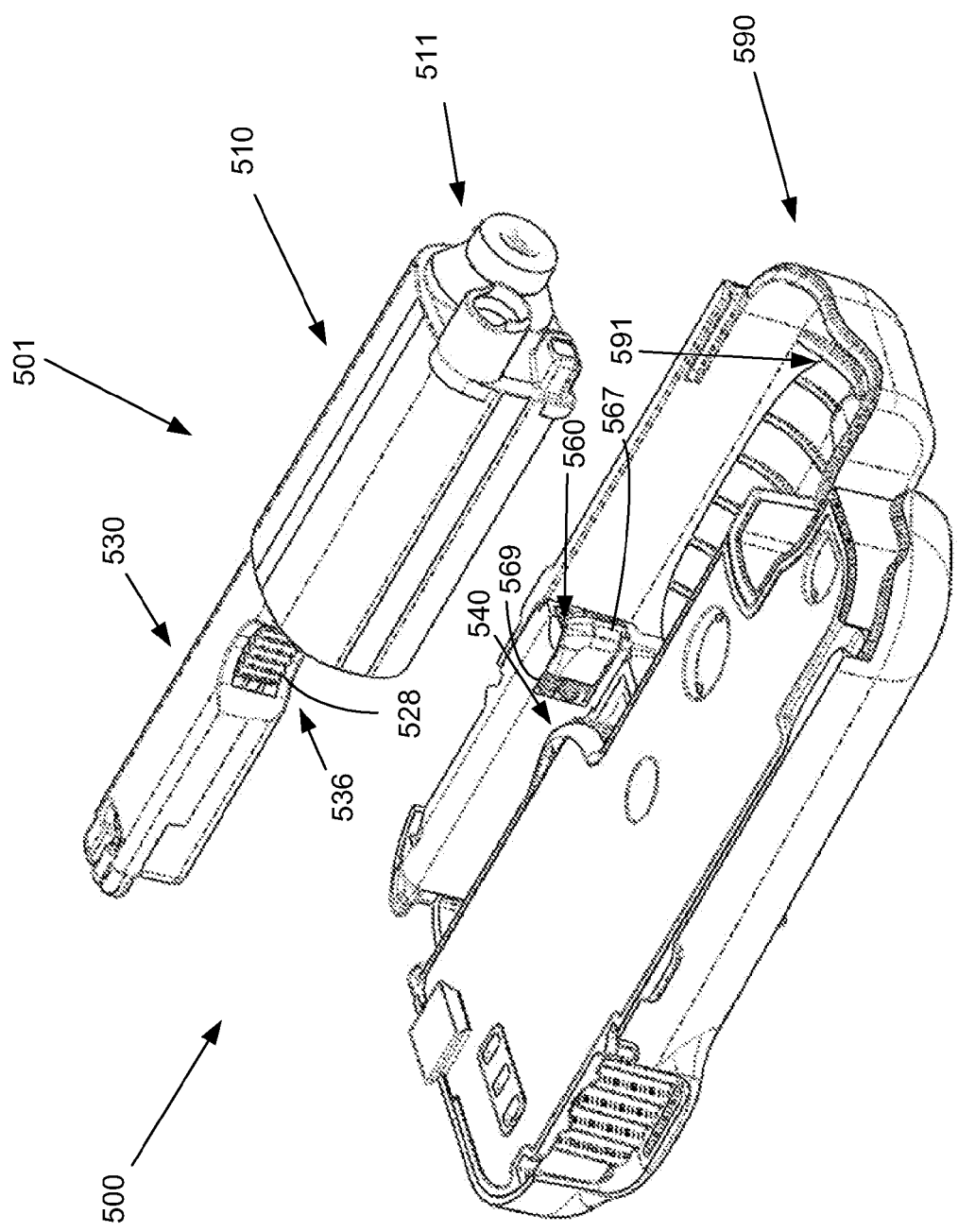

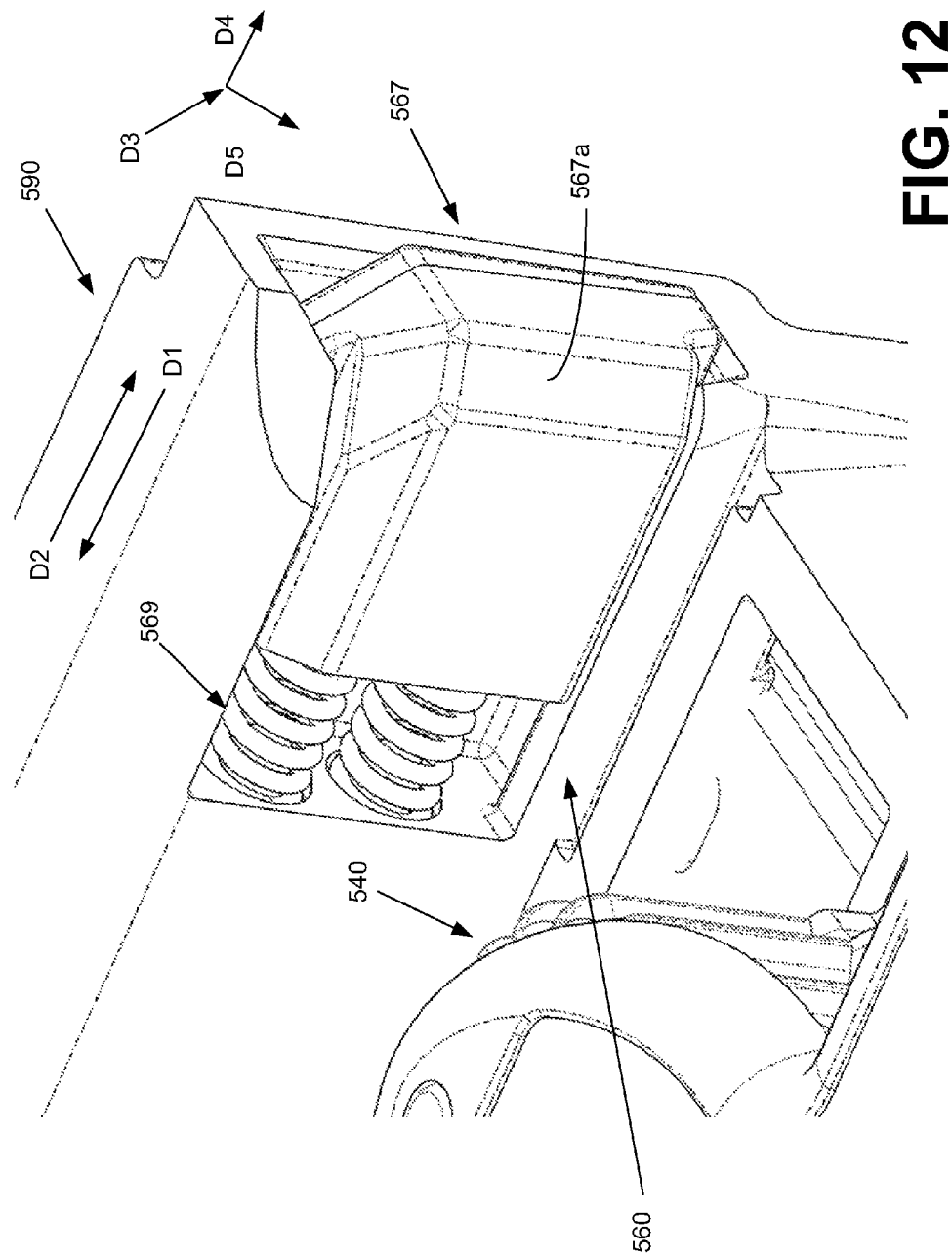

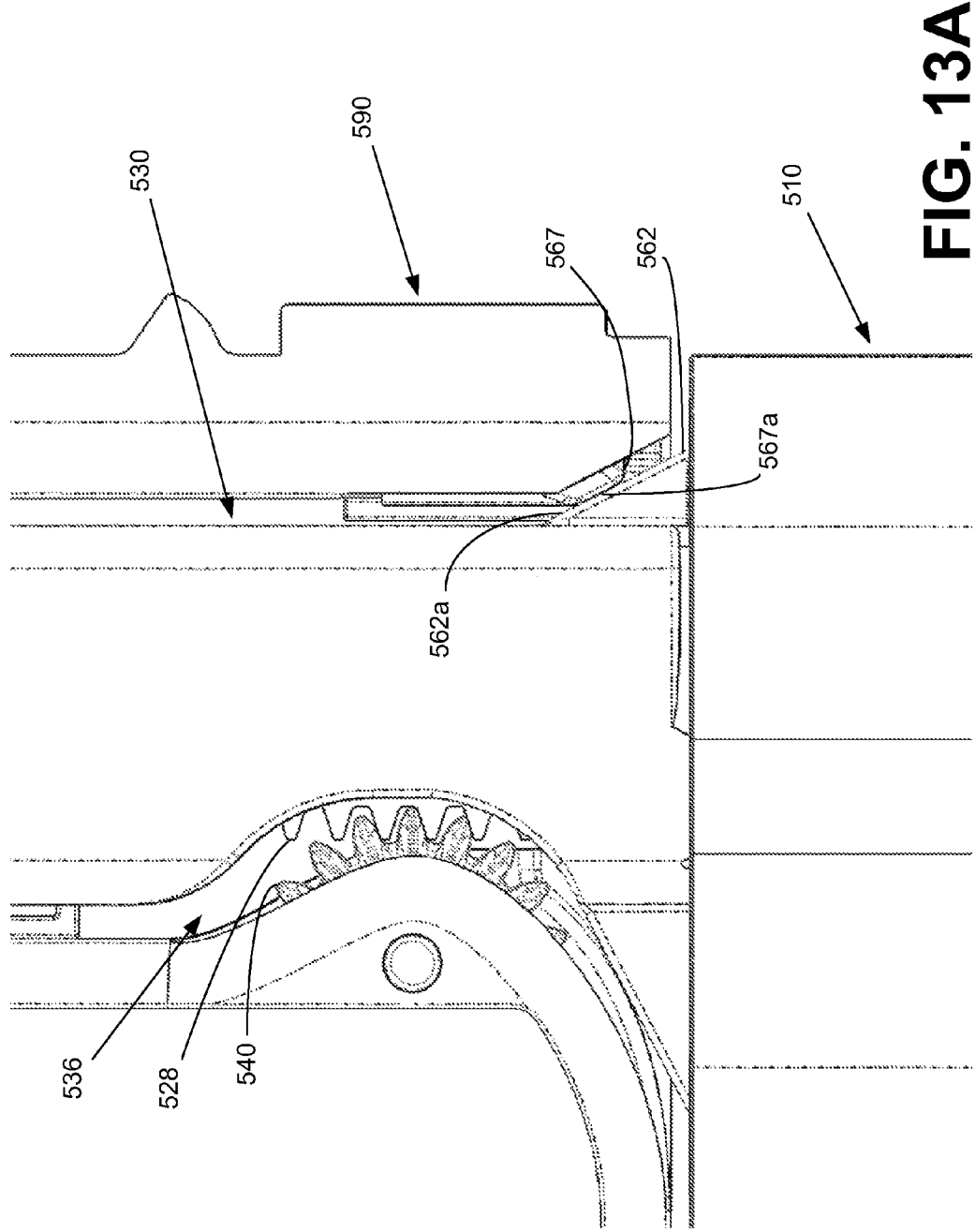

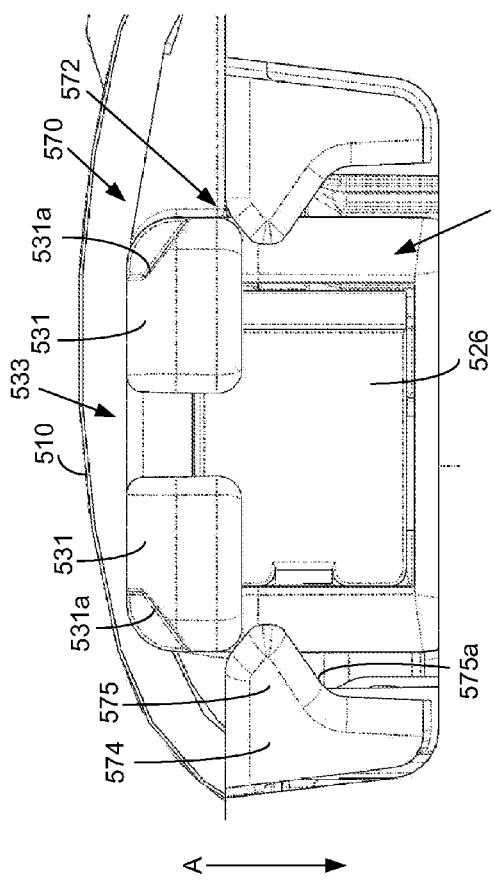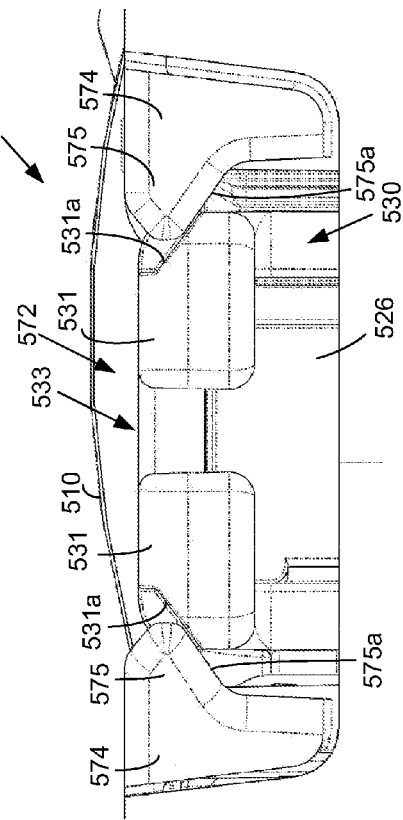

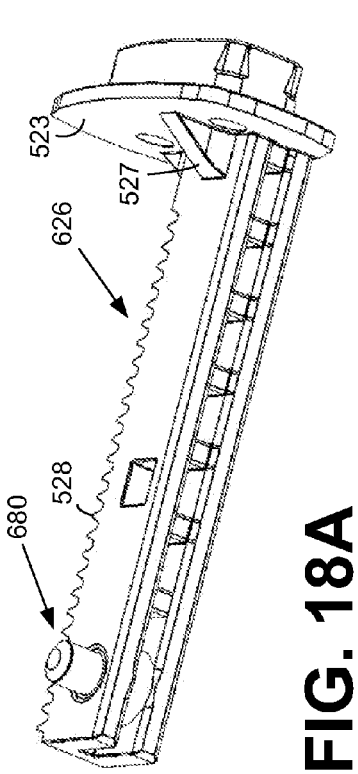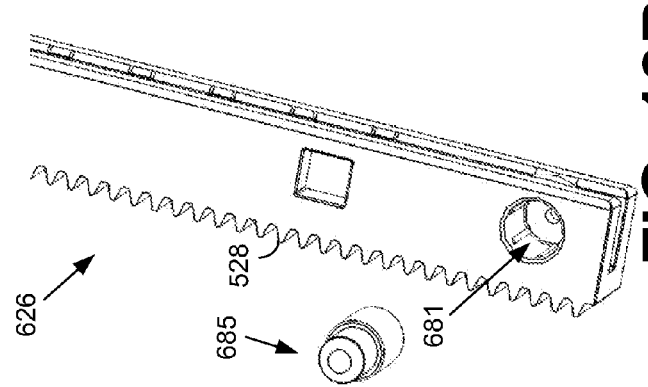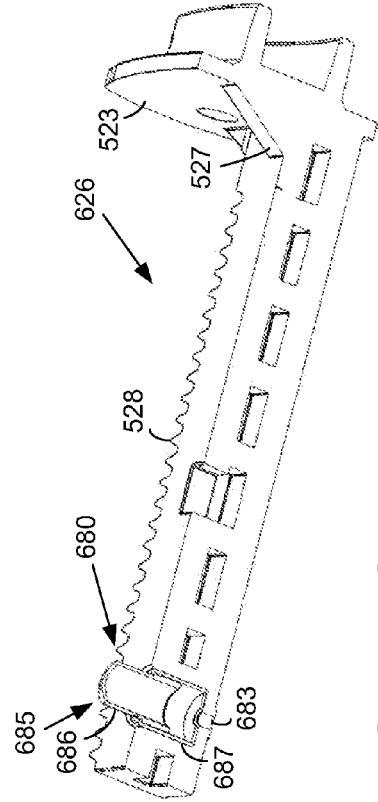

RETENTION SYSTEMS AND METHODS

CROSS-REFERENCE TO RELATED PATENT APPLICATIONS

This application is a Continuation-In-Part of U.S. application Ser. No. 12/649,172, filed Dec. 29, 2009, incorporated herein by reference in its entirety. This application is a Continuation-In-Part of U.S. application Ser. No. 12/650,378, filed Dec. 30, 2009, incorporated herein by reference in its entirety. This application is a Continuation-In-Part of U.S. application Ser. No. 12/649,619, filed Dec. 30, 2009, incorporated herein by reference in its entirety. This application is a Continuation-In-Part of U.S. application Ser. No. 12/650,287, filed Dec. 30, 2009, incorporated herein by reference in its entirety.

BACKGROUND

1. Field of the Invention

Embodiments of the present invention generally relate to retention systems and methods, and, in specific embodiments, to systems and methods for retaining of medical device system components.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A system for retaining a fluid delivery device, which may include, but is not limited to, a reservoir and a plunger arm operatively connected to a plunger head arranged for movement within the reservoir, the plunger arm having an arm portion operatively engageable with a drive member configured to move the plunger arm and the plunger head when the plunger arm and the plunger head are connected to the drive member. The system may include, but is not limited to, a rigid member and a bias member. The rigid member may be arranged for movement. The bias member may be configured to urge the rigid member toward the plunger arm to force the plunger arm against the drive member to operatively engage the plunger arm to the drive member.

In various embodiments, the system may include the plunger arm and a casing configured to support the plunger arm and to envelop at least a portion of the plunger arm. In some embodiments, the bias member may be configured to urge the rigid member toward the casing, to force the plunger arm against the drive member. In some embodiments, the casing may have an opening for allowing the arm portion of the plunger arm to operatively engage the drive member. In some embodiments, the system may include a housing configured to support the drive member, the plunger arm, the ridge member, and the bias member.

In further embodiments, the bias member may be configured to urge the rigid member such that the rigid member provides a force against the casing in a first direction to urge the plunger arm against the drive member, and in a second direction to urge the casing against a surface of the housing. The second direction may be transverse to the first direction. In yet further embodiments, the first direction may be substantially perpendicular to the second direction. In yet further embodiments, wherein the second direction may be substantially parallel to a direction in which the rigid member is urged.

In various embodiments, the rigid member may have a contact surface for engaging the casing. The contact surface may be substantially flat. In some embodiments, the casing may have a contact surface for engaging the contact surface of the rigid member. The contact surface of the casing may correspond in shape with the contact surface of the rigid member. In some embodiments, the contact surface of the rigid member may be an angled surface of less than 90 degrees relative to a direction in which the rigid member is urged.

In various embodiments, the rigid member may have a contact surface for engaging the casing. The contact surface may be substantially round. In various embodiments, the rigid member may include a wedge-shaped member.

A method of manufacturing a system for retaining a fluid delivery device, which may include (but is not limited to) a reservoir and a plunger arm operatively connected to a plunger head arranged for movement within the reservoir, the plunger arm having an arm portion operatively engageable with a drive member configured to move the plunger arm and the plunger head when the plunger arm and the plunger head are connected to the drive member, the method may include, but is not limited to, any one of or combination of: (i) arranging a rigid member for movement; and (ii) configuring a bias member to urge the rigid member toward the plunger arm to force the plunger arm against the drive member to operatively engage the plunger arm to the drive member.

A system for retaining a fluid delivery device, which may include (but is not limited to) a reservoir and a plunger arm operatively connectable to a plunger head that is moveable within the reservoir, the plunger arm having an arm portion that is configured for operative engagement to a drive member configured to move the arm portion and the plunger head when the arm portion of the plunger arm is operatively engaged to the drive. The system may include, but is not limited to, a housing and a pair of protrusions.

The housing may be configured to support the plunger arm and the reservoir, the housing having a recess for receiving the plunger arm. The pair of protrusions may be arranged around the recess to allow the plunger arm to be forced between the protrusions and moved into the recess from a position outside of the recess when a first amount of force is applied on the plunger arm toward the recess. The protrusions may be configured to prevent the plunger arm from being removed from the recess using the first amount of force when the plunger arm is in the recess. The protrusions may be configured to allow the plunger arm to be removed from the recess through the protrusions to a position outside of the recess when a second amount of force is applied on the plunger arm away from the recess, the second amount of force being greater than the first amount.

In various embodiments, each protrusion may have an upper surface that is angled in toward the recess to facilitate insertion of the plunger arm into the recess. In various embodiments, the system may include the plunger arm. The plunger arm may have a surface having an angle of less than 90° relative to an upper surface of the plunger arm for engaging each protrusion to facilitate insertion of the plunger arm between the protrusions into the recess.

In various embodiments, the system may include the plunger arm. The plunger arm may be configured to compress to fit between the protrusions as the plunger arm is inserted between the protrusions into the recess. In some embodiments, the plunger arm may include an opening that allows the plunger arm to compress to fit between the protrusions as the plunger arm is inserted between the protrusions into the recess. In some embodiments, the plunger arm may be made of a first material. The protrusions may be made of a second material that is more rigid than the first material.

In various embodiments, the system may include the plunger arm. The plunger arm may have a width dimension. The protrusions may be separated by a gap having a width dimension less than the width dimension of the plunger arm. In various embodiments, the system may include the plunger arm and a plunger arm casing configured to support the plunger arm and to envelop at least a portion of the plunger arm. In some embodiments, the plunger arm casing may have a surface having an angle of less than 90 degrees relative to an upper surface of the plunger arm casing for engaging each protrusion to facilitate insertion of the plunger arm casing between the protrusions into the recess.

In some embodiments, the plunger arm casing may be configured to compress to fit between the protrusions as the plunger arm casing is inserted between the protrusions into the recess. In further embodiments, the plunger arm casing may include an opening that allows the plunger arm casing to compress to fit between the protrusions as the plunger arm casing is inserted between the protrusions into the recess. In further embodiments, the plunger arm casing may be made of a first material. The protrusions may be made of a second material that is more rigid than the first material.

In various embodiments, the system may include the plunger arm casing. The plunger arm may have a width dimension. The protrusions may be separated by a gap having a width dimension less than the width dimension of the plunger arm casing.

A method of manufacturing a system for retaining a fluid delivery device, which may include (but is not limited to) a reservoir and a plunger arm operatively connectable to a plunger head that is moveable within the reservoir, the plunger arm having an arm portion that is configured for operative engagement to a drive member configured to move the arm portion and the plunger head when the arm portion of the plunger arm is operatively engaged to the drive, the method may include, but is not limited to, any one of or combination of: (i) configuring a housing to support the plunger arm and the reservoir, the housing having a recess for receiving the plunger arm; and (ii) arranging in the housing a pair of protrusions around the recess to allow the plunger arm to be forced between the protrusions and moved into the recess from a position outside of the recess when a first amount of force is applied on the plunger arm toward the recess, the protrusions being configured to prevent the plunger arm from being removed from the recess using the first amount of force when the plunger arm is in the recess, the protrusions further being configured to allow the plunger arm to be removed from the recess through the protrusions to a position outside of the recess when a second amount of force is applied on the plunger arm away from the recess, the second amount of force being greater than the first amount.

A delivery system for delivering fluidic media to a user may include, but is not limited to, a first housing portion, a second housing portion, a drive device, a pair of interactive elements, and electronic circuitry. The first housing portion may be adapted to be carried by a user. The second housing portion may be configured to be selectively operatively engaged with and disengaged from the first housing portion. One of the first housing portion and the second housing portion may support a reservoir having an interior volume for containing fluidic media and a plunger head moveable within the interior volume of the reservoir along an axial direction of the reservoir. The plunger head may be operatively connected to a plunger arm.

The drive device may be supported by the other of the first housing portion and the second housing portion relative to the one of the first housing portion and the second housing portion supporting the reservoir such that upon the first housing portion and the second housing portion being operatively engaged. The reservoir may be operatively coupled to the drive device to allow the drive device to move the plunger head via the plunger arm within the interior volume of the reservoir. The pair of interactive elements including a first interactive element supported on the first housing portion and a second interactive element supported on the second housing portion at a location to be interactable with the first interactive element. The first interactive element may comprise a protruding member arranged for movement along with the plunger arm and the plunger head. The protruding member may be for operatively engaging the second interactive element when the first housing portion and the second housing portion are operatively engaged. The electronic circuitry may be configured to provide a signal or a change in state in response to the protruding member interacting with the second interactive element when the first housing portion and the second housing portion are operatively engaged.

In various embodiments, the first interactive element may include a bias member configured to bias at least one of the protruding member and the second interactive element toward each other. In some embodiments, the first interactive element may include a housing containing the bias member and at least a portion of the protruding member. The housing may be fit into the plunger arm. In some embodiments, the bias member may be configured to cause the protruding member to impart a force on the second interactive element. The circuitry may be configured to provide the signal or the change in state based on the force imparted on the second interactive element.

In various embodiments, a position of the protruding member relative to the second interactive element may correspond to reservoir data. In some embodiments, the reservoir data may correspond to a volume of fluidic media in the reservoir.

In various embodiments, the second interactive element may be a sensor. In some embodiments, the sensor may be a volume sensor. In further embodiments, a position of the protruding member relative to the volume sensor may correspond to reservoir data. In yet further embodiments, the reservoir data may correspond to a volume of fluidic media in the reservoir.

In some embodiments, at least one of the first interactive element and the second interactive element may include a linear sensor. In some embodiments, the electronic circuitry may be configured to activate the sensor in response to the protruding member interacting with the second interactive element where the first housing portion and the second housing portion are operatively engaged.

In various embodiments, the protruding member may be supported on the plunger arm for movement with the plunger arm. In various embodiments, the second interactive element may include a flexible conductive membrane. The protruding member may be configured to press against the flexible conductive membrane when the first housing portion and the second housing portion are operatively engaged. The electronic circuitry may be configured to provide the signal or the change in state in response to the protruding member pressing against the flexible conductive membrane. In various embodiments, the electronic circuitry may be configured to provide the signal or the change in state in response to the protruding member moving relative to the second interactive element.

A method of manufacturing a delivery system for delivering fluidic media to a user may include, but is not limited to, any one of or combination of: (i) adapting a first housing portion to be carried by a user; (ii) configuring a second housing portion to be selectively operatively engaged with and disengaged from the first housing portion, one of the first housing portion and the second housing portion supporting a reservoir having an interior volume for containing fluidic media and a plunger head moveable within the interior volume of the reservoir along an axial direction of the reservoir, the plunger head operatively connected to a plunger arm; (iii) supporting a drive device by the other of the first housing portion and the second housing portion relative to the one of the first housing portion and the second housing portion supporting the reservoir such that upon the first housing portion and the second housing portion being operatively engaged, the reservoir operatively coupled to the drive device to allow the drive device to move the plunger head via the plunger arm within the interior volume of the reservoir; (iv) supporting a pair of interactive elements including a first interactive element supported on the first housing portion and a second interactive element supported on the second housing portion at a location to be interactable with the first interactive element, the first interactive element comprising a protruding member arranged for movement along with the plunger arm and the plunger head, the protruding member for operatively engaging the second interactive element when the first housing portion and the second housing portion are operatively engaged; and (v) configuring electronic circuitry to provide a signal or a change in state in response to the protruding member interacting with the second interactive element when the first housing portion and the second housing portion are operatively engaged.

BRIEF DESCRIPTION OF THE DRAWINGS

FIGS. 7A-7B illustrate a portion of a medical device in accordance with an embodiment of the present invention;

FIG. 11 illustrates a portion of a medical device in accordance with an embodiment of the present invention;

FIG. 12 illustrates a portion of a medical device in accordance with an embodiment of the present invention;

FIGS. 13A-13B illustrate a portion of a medical device in accordance with an embodiment of the present invention;

FIGS. 16A-16B illustrate a portion of a medical device in accordance with an embodiment of the present invention;

FIGS. 18A-18F illustrate a portion of a medical device in accordance with an embodiment of the present invention.

DETAILED DESCRIPTION

Figure 1:
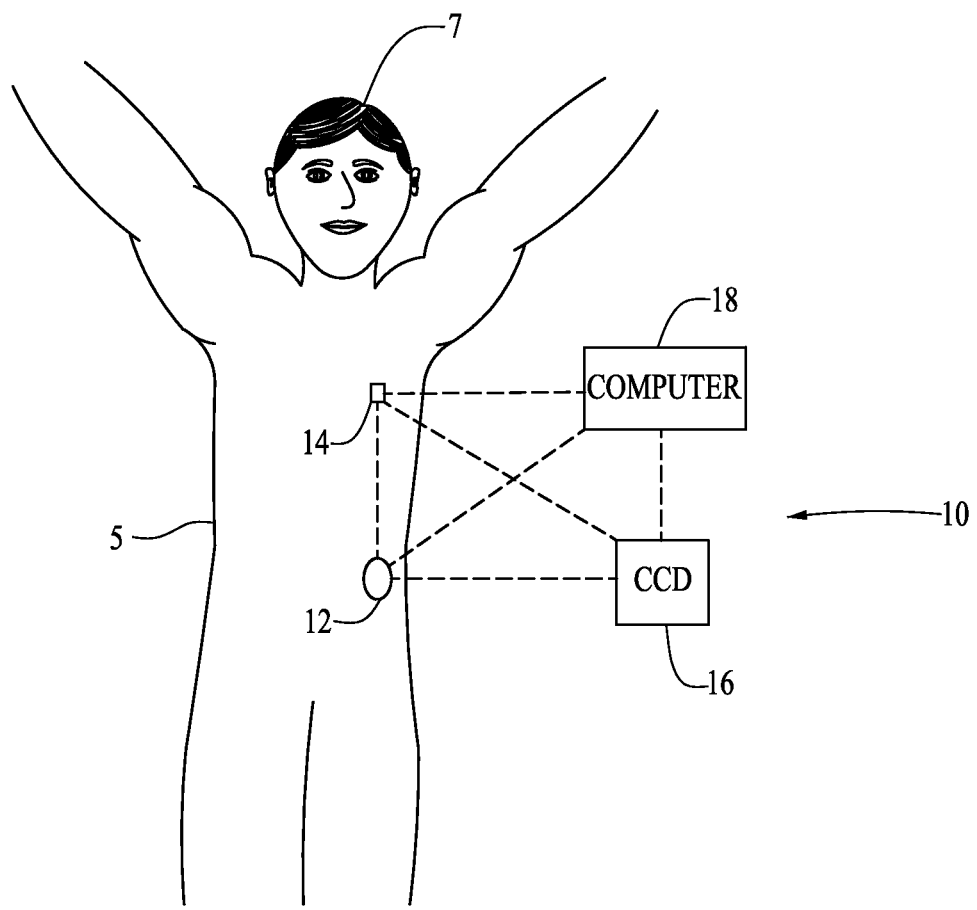
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples. It should be noted user-patient as used throughout the disclosure may include patient-user, patient, or user (e.g., a patient, a medical professional, or other treating the patient).

The system 10, the delivery device 12, the sensing device 14, the CCD 16, and/or computer 18 may be similar to (but not limited to) those described in the following U.S. Patent Applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxi) U.S. patent application Ser. No. 10/180,732, filed Jun. 26, 2002, "Communication Station And Software For Interfacing With An Infusion Pump, Analyte Monitor, Analyte Meter, And/or the like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional App. Ser. No. 61/044,269, filed Apr. 11, 2008, "Reservoir Plunger Head Systems And Methods"; (xxxvii) U.S. patent application Ser. No. 61/044,292, filed Apr. 11, 2008, "Reservoir Barrier Layer Systems And Methods"; (xxxviii) U.S. Patent Provisional App. Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (10 U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; (liii) U.S. patent application Ser. No. 12/360,813, filed Jan. 27, 2009, "Multi-Position Infusion Set Device And Process"; (liv) U.S. patent application Ser. No. 12/360,077, filed Jan. 26, 2009, "Reservoir Barrier Layer Systems And Methods"; (lv) U.S. patent application Ser. No. 12/417,976, filed Apr. 3, 2009, "Reservoir Plunger Head Systems And Methods"; (lvi) U.S. patent application Ser. No. 12/553,038, filed Sep. 2, 2009, "Insertion Device Systems And Methods"; (lvii) U.S. patent application Ser. No. 12/499,283, filed Jul. 8, 2009, "Reservoir Filling Systems And Methods"; (lviii) U.S. patent application Ser. No. 12/537,579, filed Aug. 7, 2009, "Transfer Guard Systems And Methods"; (lix) U.S. patent application Ser. No. 12/649,619, filed Dec. 30, 2009, "Alignment Systems And Methods"; (lx) Ser. No. 12/650,287, filed Dec. 30, 2009, "Engagement And Sensing Systems And Methods"; (lxi) U.S. patent application Ser. No. 12/650,378, filed Dec. 30, 2009, "Connection And Alignment Systems And Methods"; (lxii) U.S. patent application Ser. No. 12/405,840, filed Mar. 17, 2009, "Sterile Device And Method For Producing Same"; (lxiii) U.S. patent application Ser. No. 12/411,236, filed Mar. 25, 2009, "Adhesive Patch Systems And Methods"; (lxiv) U.S. patent application Ser. No. 12/419,188, filed Apr. 6, 2009, "Implantable Sensor Electrodes and Electronic Circuitry"; (lxv) U.S. patent application Ser. No. 12/411,247, filed Mar. 25, 2009, "Adhesive Patch Systems And Methods"; (lxvi) U.S. patent application Ser. No. 12/649,172, filed Dec. 29, 2009, "Insertion Device Systems And Methods"; (lxvii) U.S. patent application Ser. No. 12/497,345, filed Jul. 2, 2009, "Infusion Medium Delivery Device And Method With Drive Device For Driving Plunger In Reservoir"; (lxviii) U.S. patent application Ser. No. 12/490,006, filed Jun. 23, 2009, "Safety Limits For Closed-Loop Infusion Pump Control"; (lxix) U.S. patent application Ser. No. 12/533,942, filed Jul. 31, 2009, "Reservoir Barrier Layer Systems And Methods"; (lxx) U.S. patent application Ser. No. 12/547,315, filed Aug. 25, 2009, "Reservoir Barrier Layer Systems And Methods," all of which are herein incorporated by reference in their entirety. In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
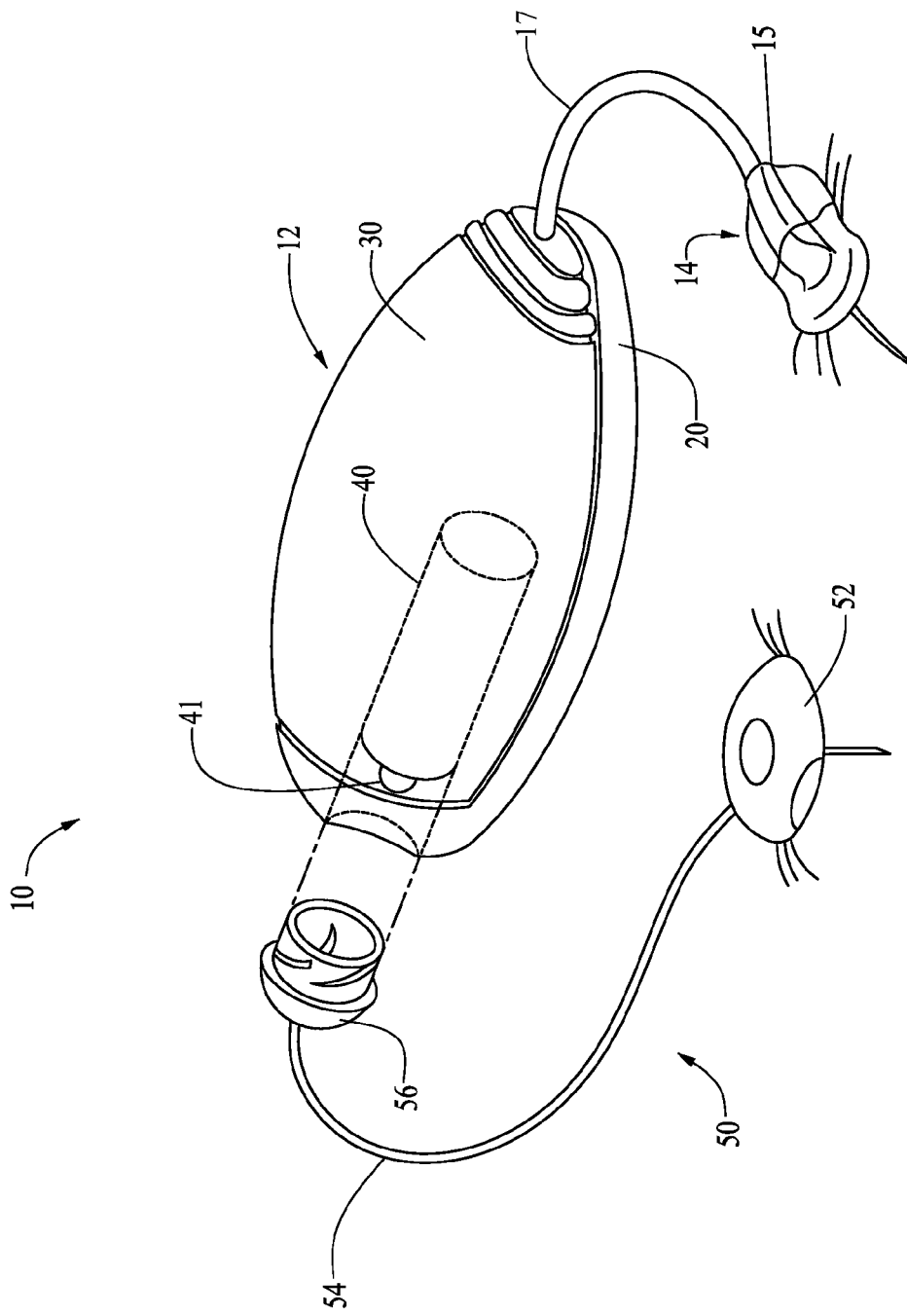
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, in a friction fit connection, in a slidable connection, and/or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2) that may include a motor and a drive device linkage portion. The drive device may be configured to apply a force to fluidic media within the reservoir system 40 to force fluidic media out of the reservoir system 40 and into an infusion path, such as the infusion path 50, for delivery to a user-patient. For example, in some embodiments, an electrically-driven motor 84 (refer to FIGS. 5B and 5C) may be mounted within the durable housing 30 with appropriate linkage for operatively coupling the motor 84 to a plunger arm (refer to FIGS. 6A-6C) connected to a plunger head (refer to FIGS. 6A-6C) arranged within the reservoir system 40. The electrically-driven motor may be configured to drive the plunger head in a direction to force fluidic media out of the port 41 of the reservoir system 40 and to the user-patient.

Also, in some embodiments, the motor 84 may be controllable to reverse direction to move the plunger arm 60 and the plunger head to cause fluid to be drawn into the reservoir system 40 from a patient. The motor 84 may be arranged within the durable housing 30 and the reservoir system 40 may be correspondingly arranged on the disposable housing 20, such that the operable engagement of the motor 84 with the plunger head, through the appropriate linkage, occurs automatically upon the user-patient connecting the durable housing 30 with the disposable housing 20 of the delivery device 12. Further examples of linkage and control structures may be found in, but are not limited to, U.S. patent application Ser. No. 09/813,660, filed Mar. 21, 2001, entitled "Control Tabs for Infusion Devices and Methods of Using the Same"; U.S. Patent Pub. No. 2006/0264894 (application Ser. No. 11/211,095), filed Aug. 23, 2005, entitled "Infusion Device and Method with Disposable Portion"; U.S. patent application Ser. No. 11/210,467, filed Aug. 23, 2005, entitled "Infusion Device and Method With Drive In Separable Durable Housing Portion"; U.S. patent application Ser. No. 11/211,150, filed Aug. 23, 2005, entitled "Pump Assembly and Method For Infusion Device"; U.S. patent application Ser. No. 11/210,455, filed Aug. 23, 2005, entitled "Reservoir Support And Method For Infusion Device"; and U.S. Pat. No. 6,485,465, filed Mar. 27, 2001, entitled "Methods, Apparatuses, and Uses for Infusion Pump Fluid Pressure and Force Detection," all of which are incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
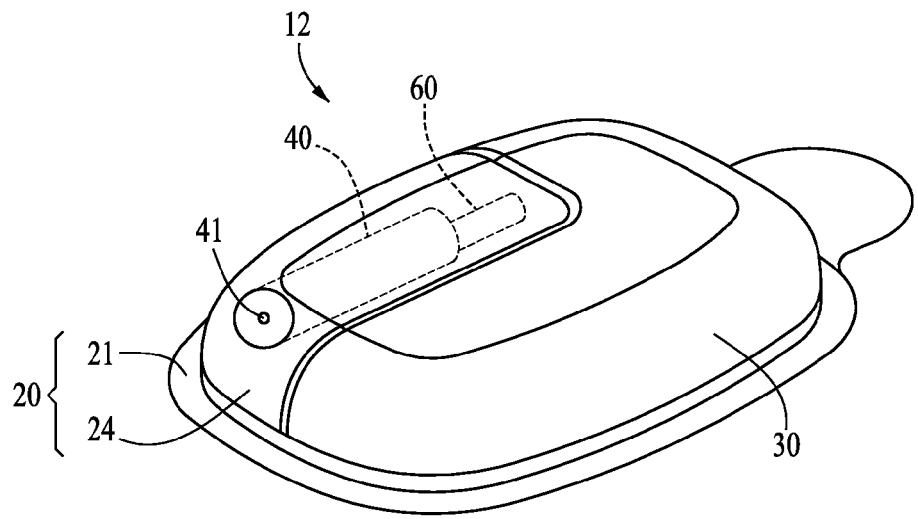
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
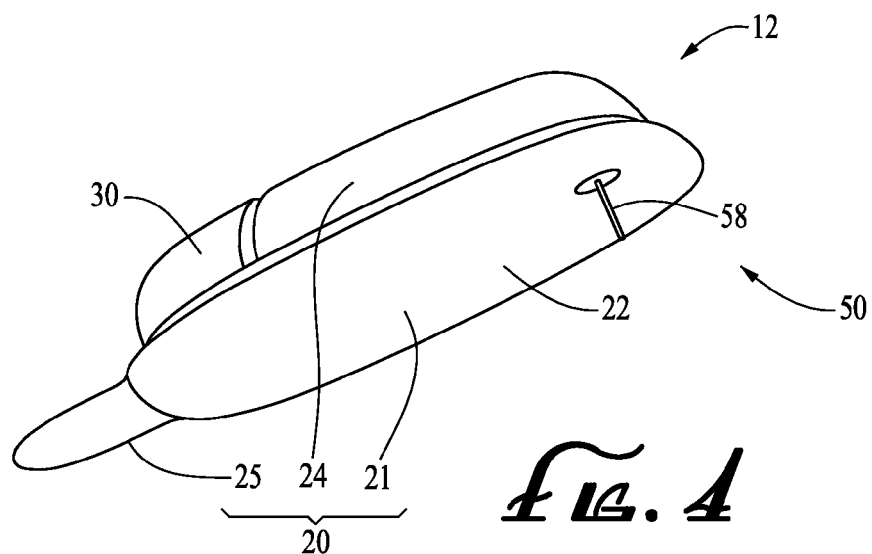
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place with one end of the cannula located within the body of the user-patient and the other end of the cannula in fluid flow connection with fluidic media within the reservoir system 40. Accordingly, fluidic media may be conveyed from the reservoir system 40 to the body of the user-patient.

Figure 5A:
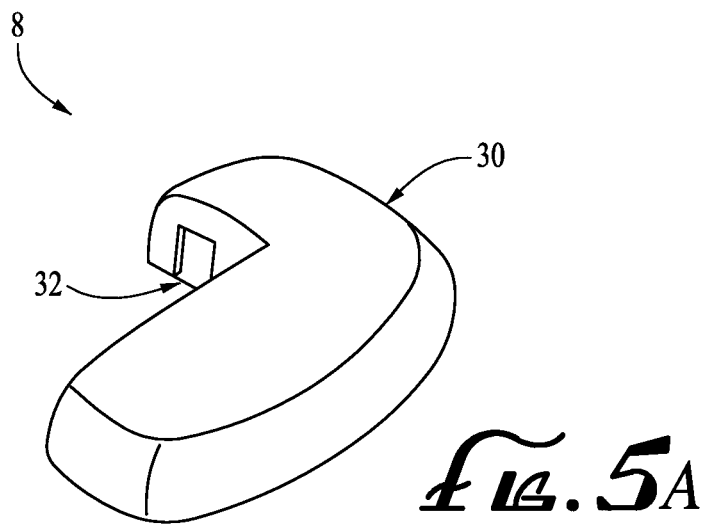
FIG. 5A illustrates a durable portion of a delivery device in accordance with an embodiment of the present invention.
Figure 5B:
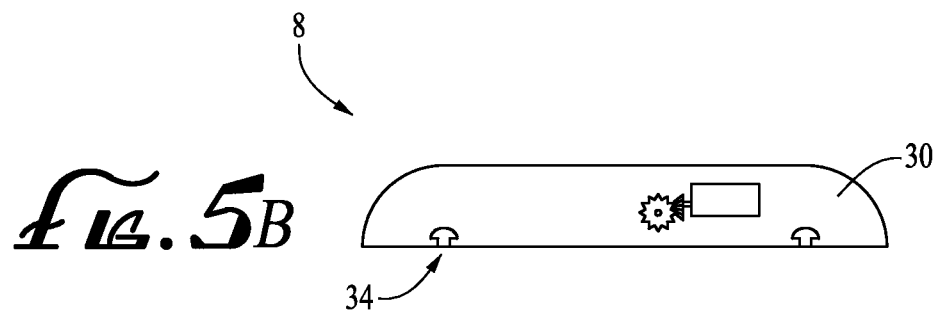
FIG. 5B illustrates a section view of a durable portion of a delivery device in accordance with an embodiment of the present invention.
Figure 5C:
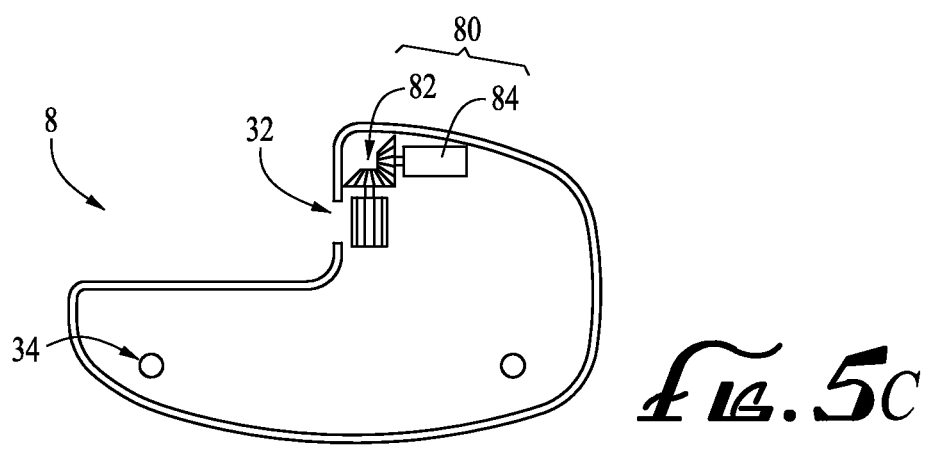
FIG. 5C illustrates a section view of a durable portion of a delivery device in accordance with an embodiment of the present invention.

FIG. 5A illustrates a durable portion 8 of the delivery device 12 (e.g., FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (e.g., FIG. 3).

Figure 6A:
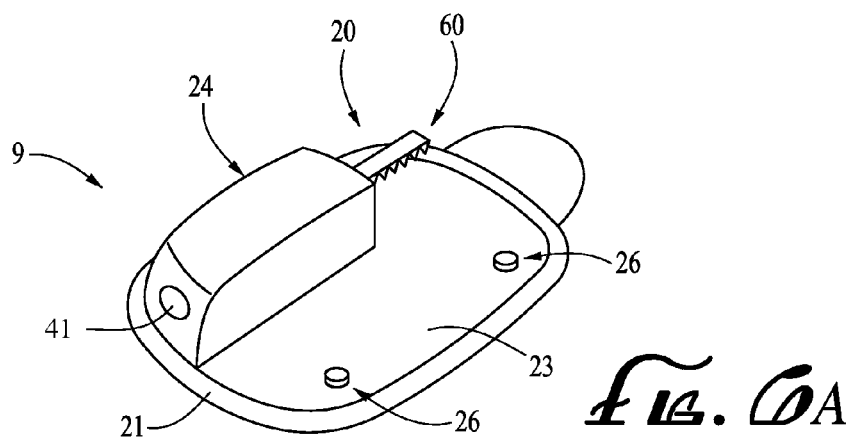
FIG. 6A illustrates a disposable portion of a delivery device in accordance with an embodiment of the present invention.
Figure 6B:
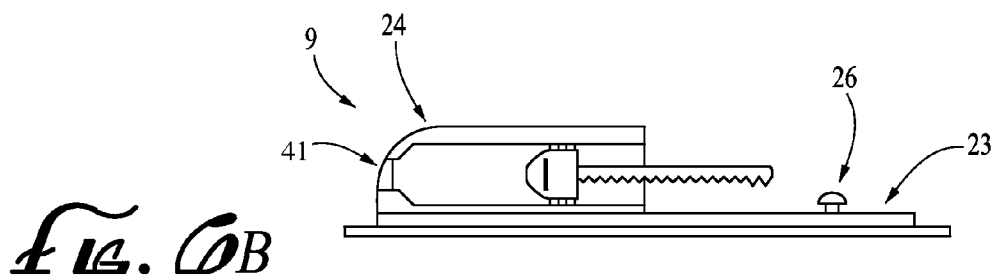
FIG. 6B illustrates a section view of a disposable portion of a delivery device in accordance with an embodiment of the present invention.
Figure 6C:
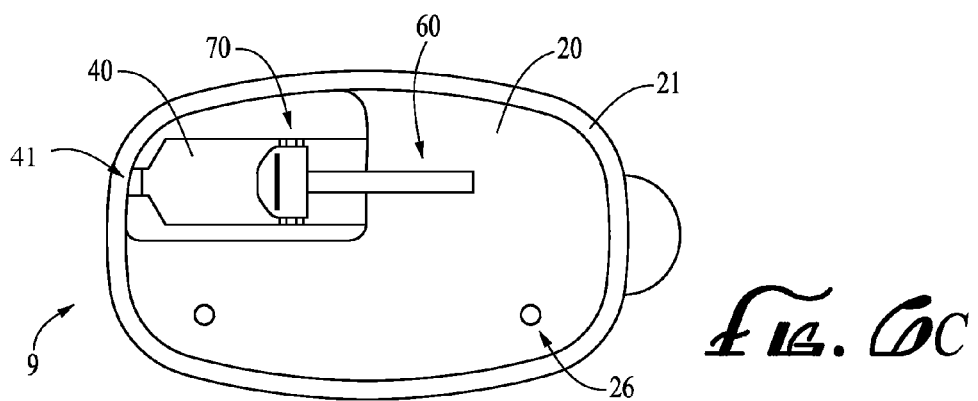
FIG. 6C illustrates a section view of a disposable portion of a delivery device in accordance with an embodiment of the present invention.

FIG. 6A illustrates a disposable portion 9 of the delivery device 12 (e.g., FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. The plunger head 70 may be made of Bromobutyl rubber, silicone rubber, or any other suitable material and/or any derivative thereof. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (e.g., FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (e.g., FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82. Accordingly, the plunger arm 60 may be moved to cause the plunger head 70 to move within the reservoir system 40. When the interior volume of the reservoir system 40 is sufficiently filled with fluidic media and an infusion path is provided from the reservoir system 40 to the body of the user-patient, the plunger head 70 may be moved within the reservoir system 40 to force fluidic media from the reservoir system 40 to the user-patient via the infusion path.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (e.g., FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; (iv) an amount of contents in the reservoir system 40; or the like. In some embodiments, the delivery device 12 may include the reservoir status circuitry, and the reservoir status circuitry may be configured to read data from the reservoir circuitry when the reservoir system 40 is inserted into the disposable portion 9.

In various embodiments, the reservoir status circuitry may be further configured to store data to the reservoir circuitry after at least some of the contents of the reservoir system 40 have been transferred out of the reservoir system 40 to update information in the reservoir circuitry. Such information may be related to, but is not limited to, an amount of fluidic media remaining in the reservoir system 40, an amount of fluidic media already delivered, plunger head 60 location, pressure within the reservoir system, or the like.

In some embodiments, the reservoir status circuitry may be configured to store data to the reservoir circuitry to update information in the reservoir circuitry related to an amount of contents remaining in the reservoir system 40 when the reservoir system 40 is inserted into the disposable portion 9. In some embodiments, the delivery device 12 may include the reservoir status circuitry and the reservoir system 40 may include the reservoir circuitry, and the reservoir status circuitry may selectively inhibit use of the delivery device 12 or may selectively provide a warning signal based on information read by the reservoir status circuitry from the reservoir circuitry.

Various embodiments relate, generally, to needle inserter or inserting devices and methods and medical devices, such as, but not limited to sensors, monitors and infusion medium delivery systems, devices and methods that include such needle-inserting devices and methods. The needle-inserting device and method may operate to insert a needle or cannula through skin of a user-patient, for example, to provide a fluid flow path for conveying an infusion medium through a hollow channel in the needle or cannula and into the user-patient and/or to convey a fluid from the user-patient to one or more sensor elements. Embodiments of the present invention may be configured, as described herein, to provide a reliable, cost effective, and easy-to-use mechanism for inserting a needle or cannula to a specific depth into a user-patient with minimal traumatic effect.

In addition, embodiments may be configured to establish a contiguous fluid flow passage for fluid transfer between a reservoir and the user-patient when the hollow needle or cannula is inserted into the user-patient. Needle-inserting devices according to embodiments of the present invention may be used with, connectable to and disconnectable from, or incorporated in a portion of an infusion medium delivery system. For example, a needle-inserting device may be connectable to a base structure of a pump-type delivery device for insertion of a needle, after which the needle-inserting device may be removed from the base structure, whereupon a further housing portion of the delivery device (containing components such as, but not limited to, a reservoir and pump or drive device) may be coupled to the base structure for operation.

Alternatively, the needle-inserting device may be incorporated into the further housing portion that contains other components as described above. In yet other embodiments, the needle-inserting device may be connectable to (and releasable from) or incorporated within an injection site module or other housing that connects, for example, by flexible tubing, to other components of a medical device (such as, but not limited to an infusion medium delivery device). In yet other embodiments, needle inserter devices may be configured for use with systems other than infusion medium delivery systems, such as, but not limited to sensor and monitor systems, or the like.

FIGS. 7A-10 illustrate a reservoir system 501 that may be employed as an embodiment of a reservoir system (e.g., 40 in FIGS. 1-6C) discussed above, for delivering fluidic media in accordance with an embodiment of the present invention. Although the reservoir system 501 may be similar or used with the embodiments of FIGS. 1-6C, it should be understood that the reservoir system 501 may also include some or all of the same components and operate in a manner similar to that shown and described in the embodiments of FIGS. 11-18F. In addition, some or all of the features shown in FIGS. 1-6C and 11-18F may be combined in various ways and included in the embodiments shown in FIGS. 7A-10. Likewise, it should be understood that any of the features of the embodiments of FIGS. 7A-10 may be combined or otherwise incorporated into any of the other embodiments of FIGS. 7A-10 as well as any other embodiment herein discussed. Also, the reservoir system 501 may be employed or used with other types of delivery device systems and/or components other than those described in the disclosure. In various embodiments, the reservoir system 501 may be employed with a medical device 500.

The reservoir system 501 may include, but is not limited to, a container or body 510 of the reservoir, a plunger head 520, a plunger arm 526, and a plunger arm casing 530. The reservoir body 510 may have an interior volume 512 for containing fluidic media. The reservoir body 510 may have a first port 514 for allowing fluidic media to flow into the interior volume 512 of the reservoir body 510. The reservoir body 510 may have a second port 516 for expelling fluidic media contained in the interior volume 512 of the reservoir body 510. In various embodiments, one of the first port 514 and the second port 516 of the reservoir body 510 may be for allowing fluidic media to flow into the interior volume 512 of the reservoir body 510 and for expelling fluidic media contained in the interior volume 512 of the reservoir body 510. In various embodiments, the reservoir body 510 may be made of various suitable materials, including, but not limited to, glass, plastic, TOPAS® polymers (or any other cyclic olefin copolymer (or polymer)), or the like.

The plunger head 520 may be located within the reservoir body 510 and may be moveable in an axial direction of the reservoir body 510 to expand (e.g., FIG. 7A) or contract (e.g., FIG. 7B) the interior volume 512 of the reservoir body 510. The plunger head 520 may be advanced within the reservoir body 510 to expel fluidic media contained in the interior volume 512 of the reservoir body 510 out the second port 516 of the reservoir body 510. The plunger head 520 may be made of Bromobutyl rubber, silicone rubber, or any other suitable material and/or any derivative thereof. The plunger head 520 may have a front portion 522 and a rear portion 523.

The front portion 522 of the plunger head 520 may be in contact with fluidic media contained in the interior volume 512 of the reservoir body 510. In some embodiments, the front portion 522 of the plunger head 520 may comprise a material compatible with fluidic media contained in the interior volume 512 of the reservoir body 510. In such embodiments, any number of the remaining portions of the plunger head 520, such as the rear portion 523 of the plunger head 520, the plunger arm 526, and the plunger arm casing 530 may be made of a similar material or of any suitable material, including, but not limited to, materials that need not be compatible with fluidic media contained in the interior volume 512 of the reservoir body 510. Such materials may be selected based on strength, cost, or the like.

In some embodiments, where the interior volume 512 of the reservoir body 510 is for containing insulin, the front portion 522 of the plunger head 520 may comprise an insulin compatible material, such as, but not limited to, polyethylene, or the like. In such embodiments, any number of the remaining portions of the plunger head 520, such as the rear portion 523 of the plunger head 520, the plunger arm 526, and the plunger arm casing 530, may be made of an insulin compatible material, which may be the same or different from that of the front portion 522, or of any suitable material, including, but not limited to, materials that need not be compatible with insulin.

In some embodiments, the front portion 522 of the plunger head 520 may be removably attachable to the plunger head 520 (or the rear portion 523). For example, the front portion 522 of the plunger head 520 may have one or more tabs 521 configured to fit into one or more apertures (not shown) located on the plunger head 520. Alternatively, the front portion 522 of the plunger head 520 may have one or more apertures (not shown) for receiving one or more tabs (not shown) provided on the plunger head 520 (or the rear portion 523). In various embodiments, the front portion 522 of the plunger head 520 may be secured to the plunger head 520 in any suitable manner, such as, but not limited to, a snap-fitting, an adhesive, friction fitting, laser welding, magnetic coupling, or the like.

The rear portion 523 of the plunger head 520 may be connected or connectable to an end of the plunger arm 526 in any suitable manner. For example, the rear portion 523 of the plunger head 520 may include an aperture (not shown) for receiving a tab (not shown) or the like of the plunger arm 526. The tab (not shown) may be snap-fit into the aperture (not shown) to connect the plunger arm 526 to the rear portion 523 of the plunger head 520. Alternatively, the rear portion 523 of the plunger head 520 may have one or more tabs (not shown) configured to fit into one or more apertures (not shown) located on the plunger arm 526. In various other embodiments, the plunger arm 526 may be connected to the plunger head 520 and/or the rear portion 523 of the plunger head 520 in any suitable manner, such as, but not limited to, an adhesive, friction fitting, laser welding, magnetic coupling, or the like.

The plunger arm 526 may be moveable in an axial direction within the plunger arm casing 530 and the reservoir body 510. In some embodiments, the plunger arm 526 and the rear portion 523 of the plunger head 520 may be integral to one another. In other embodiments, the plunger arm 526 and the rear portion 523 of the plunger head 520 may be separate components.

The plunger arm 526 may include an engagement side 528 for operatively engaging a drive member 540, drive linkage, or the like. For example, the engagement side 528 of the plunger arm 526 and the drive member 540 may be complementing gears, complementing threaded members, or the like, that may operatively engage one another. The drive member 540 may be a drive screw, drive rack, or the like. The drive member 540 may be connected to a motor (not shown) to move the drive member 540 to cause the plunger arm 526 to move within the plunger arm casing 530 and the reservoir body 510. Accordingly, the drive motor may actuate the plunger arm 526 to move within the reservoir body 510 to expand and contact the interior volume 512 of the reservoir body 510.

The plunger arm casing 530 may be for supporting the plunger arm 526 as the plunger arm 526 is moved along the plunger arm casing 530. At least one side of the plunger arm 526 may be in contact with one or more interior sides of the plunger arm casing 530. In some embodiments, the plunger arm casing 530 may be for aligning the plunger arm 526 as the plunger arm 526 is moved along the reservoir body 510, for example by the drive member 540. The plunger arm casing 530 may ensure linear alignment of the plunger arm 526 relative to the longitudinal axis of the reservoir body 510 and/or perpendicularity of the plunger head 520 relative to the reservoir body 510 as the plunger arm 526 and/or the plunger head 520 enters and/or moves within the reservoir body 510.

In various embodiments, the plunger arm casing 530 may be sized and configured to substantially envelop the plunger arm 526, for example in a case where the plunger head 520 is in a position substantially near the back end of the reservoir body 510 (e.g., FIG. 7A). Accordingly, the plunger head 520 may be moveable from that position toward a front end of the reservoir body 510 (e.g., FIG. 7B) in which case a portion of the plunger arm 526 may be located within the reservoir body 510 and a further portion of the plunger arm 526 may be located within the plunger arm casing 530. Thus in some embodiments, the plunger arm 526 may be located within the reservoir body 510 and/or the plunger arm casing 530 during use of the reservoir system 501 by the user-patient (e.g., during delivery of fluidic media to the user-patient).

Figure 8:
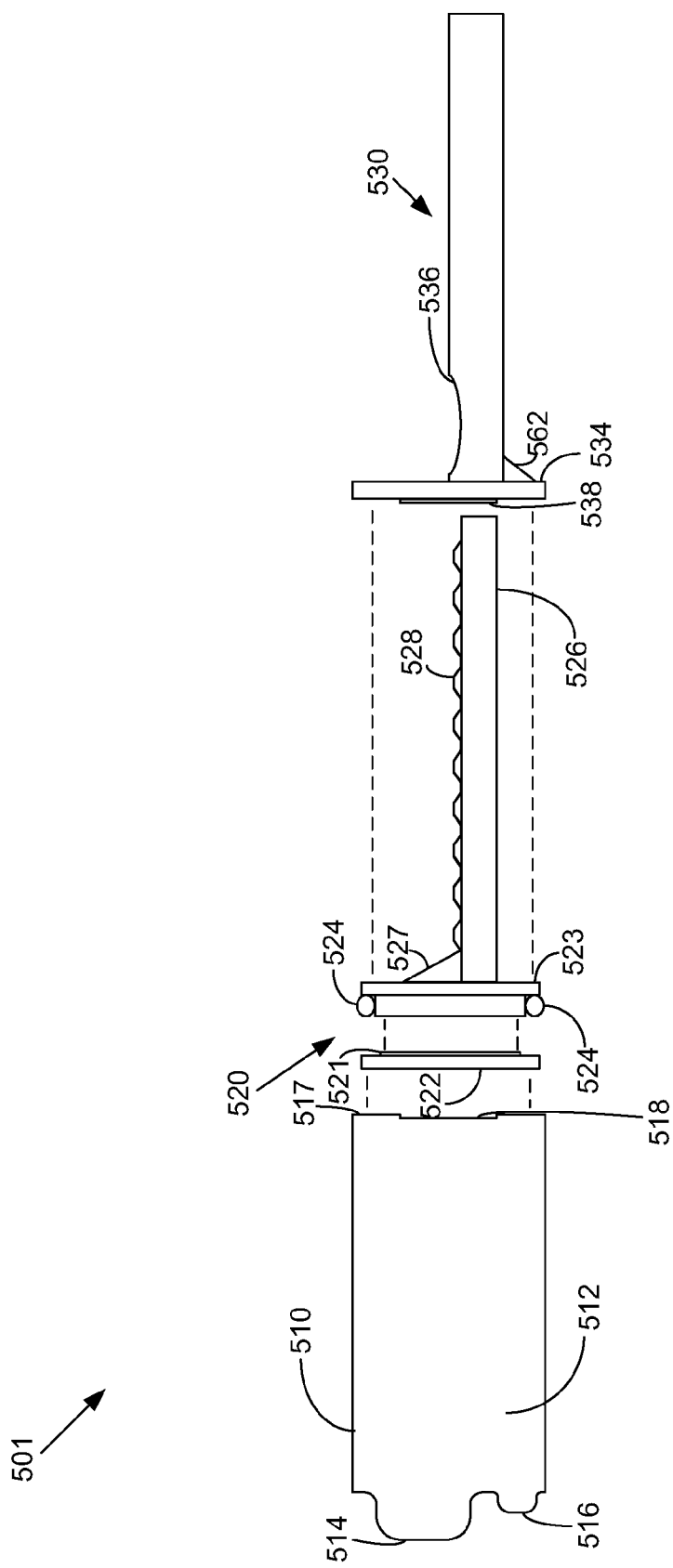
FIG. 8 illustrates a portion of a medical device in accordance with an embodiment of the present invention.

With reference to FIGS. 7A-8, in some embodiments, the plunger arm casing 530 may have a feature such as an opening 536 for allowing a portion of the engagement side 528 of the plunger arm 526 to operatively engage the drive member 540. In such embodiments, the plunger arm 526 may be surrounded by the plunger arm casing 530 and/or the reservoir body 510. Accordingly in such embodiments, only the portion of the engagement side 528 of the plunger arm 526 exposed by the opening 536 may be free from (i.e., not covered by) the plunger arm casing 530 and/or the reservoir body 510 for operable engagement with the drive member 540. This may allow the drive member 540 to operatively engage the engagement side 528 of the plunger arm 526 while the plunger arm 526 or a portion thereof remains in the plunger arm casing 530 and/or the reservoir body 510.

The reservoir system 501 may include a reservoir cover (or casing) 534 that may be sized and configured to cover an end 517 of the reservoir body 510. For example, in a case where the first port 514 and the second port 516 is located on a first end of the reservoir body 510, a second end opposite the first end may be the end 517 of the reservoir body 510 covered by the reservoir cover 534. The reservoir cover 534 may be integral with the plunger arm casing 530.

In other embodiments, the reservoir cover 534 may be separate from the plunger arm casing 530. For example, the reservoir cover 534 may be removably attachable to the plunger arm casing 530. In such embodiments, the reservoir cover 534 may be connected to or connectable to the plunger arm casing 530 in any suitable manner, such as those previously described.

In some embodiments, the end 517 of the reservoir body 510 may be open. The reservoir cover 534 may cover the open end 517 of the reservoir body 510 or be configured to fit within the open end 517 of the reservoir body 510 to seal or close the open end 517 of the reservoir body 510. The open end 517 may allow the plunger head 520 and/or at least a portion of the plunger arm 526 attached to the plunger head 520 to be insertable into the reservoir body 510, for example, before the reservoir cover 534 is placed in/on the reservoir body 510 to cover the open end 517 of the reservoir body 510.

For example, the reservoir cover 534 may include one or more tabs 538 sized and configured to fit within one or more recesses 518 on end 517 of the reservoir body 510, to fit the reservoir cover 534 to the reservoir body 510, to substantially close the reservoir body 510 after the plunger head 520 and/or at least a portion of the plunger arm 526 have been placed in the reservoir body 510. Alternatively, the reservoir cover 534 may include one or more recesses (not shown) for receiving one or more tabs (not shown) of the reservoir body 510 to fit the reservoir cover 534 to the reservoir body 510. However, the reservoir cover 534 may be connected to or connectable to the reservoir body 510 in any suitable manner, such as those previously described.

In some embodiments, the reservoir cover 534 and/or the plunger arm casing 530 may be configured for minimizing an expansion of the reservoir body 510, for example, as pressure within the reservoir body 510 increases during use. In such embodiments, by fitting the reservoir cover 534 to the back of the reservoir body 510 in one or more dimensions, the reservoir cover 534 may help to retain a shape of the reservoir body 510.

A seal member 524, such as an o-ring or the like, may be positioned between the reservoir body 510 and a portion of the plunger head 520. The interior volume 512 of the reservoir body 510 may be on one side of the seal member 524. The reservoir body 510 may have a chamber 552 located on an opposite side of the seal member 524 from the interior volume 512 of the reservoir body 510.

The seal member 524 may be for substantially preventing fluidic media from flowing from the interior volume 512 of the reservoir body 510 to the chamber 552 of the reservoir body 510. The chamber 552 of the reservoir body 510 may be located between the seal member 524 and the reservoir cover 534 in a case where the plunger head 520 is in the reservoir body 510 and the reservoir cover 534 and/or the plunger arm casing 530 are fitted or otherwise attached to the reservoir body 510. In some embodiments, the seal member 524 may be located between the front portion 522 and the rear portion 523 of the plunger head 520.

In some embodiments, the reservoir system 501 may include at least one support flange 527 positioned on the plunger arm 526 and the rear portion 523 of the plunger head 520. The support flange 527 may provide additional structural strength to the plunger arm 526 and/or the plunger head 520. For example, the support flange 527 may have a triangular configuration and be positioned with one side of the support flange 527 connected to a top surface of the plunger arm 526 and a second side of the support flange 527 connected to the rear portion 523 of the plunger head 520. In addition or alternatively, a second support flange (not shown) may be positioned with one side of the second support flange (not shown) connected to a side surface of the plunger arm 526 and a second side of the second support flange (not shown) connected to the rear portion 523 of the plunger head 520.

Figure 9:
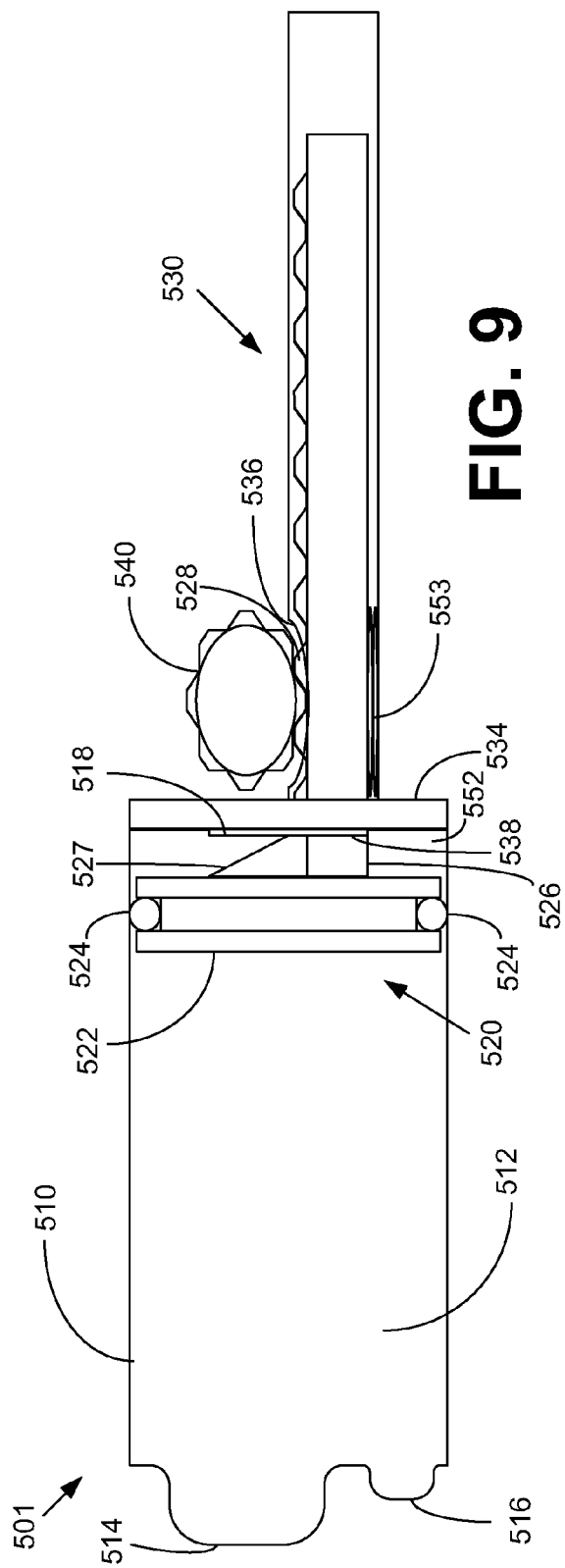
FIG. 9 illustrates a portion of a medical device in accordance with an embodiment of the present invention.

In some embodiments, such as the embodiment illustrated in FIG. 9, the reservoir system 501 may include a bias member 553. The bias member 553 may comprise, but is not limited to, a spring or the like. The bias member 553 may be positioned between the plunger arm casing 530 and the plunger arm 526. The bias member 553 may be configured to force the plunger arm 526 against the drive member 540 to allow the plunger arm 526 to operatively engage the drive 540.

Figure 10:
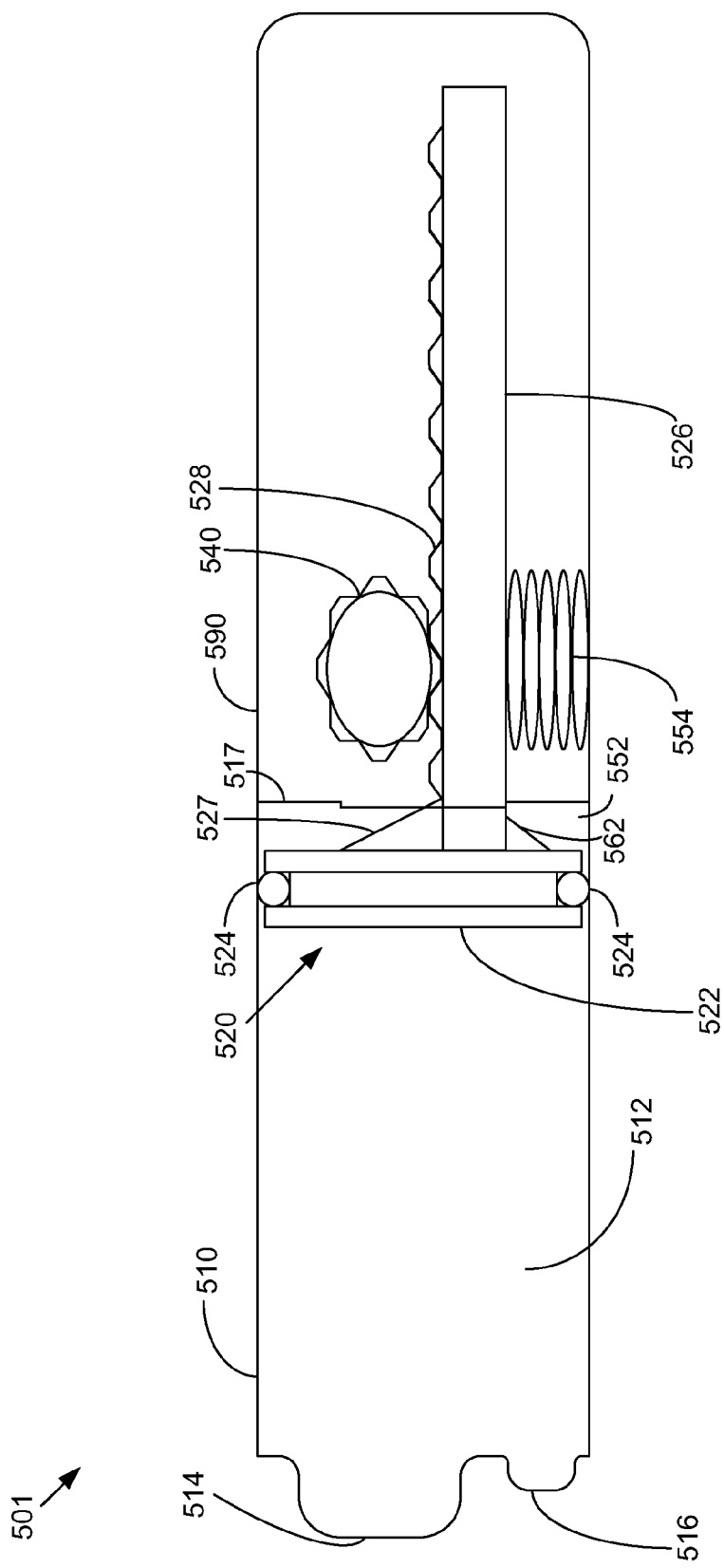
FIG. 10 illustrates a portion of a medical device in accordance with an embodiment of the present invention.
Figure 13B:
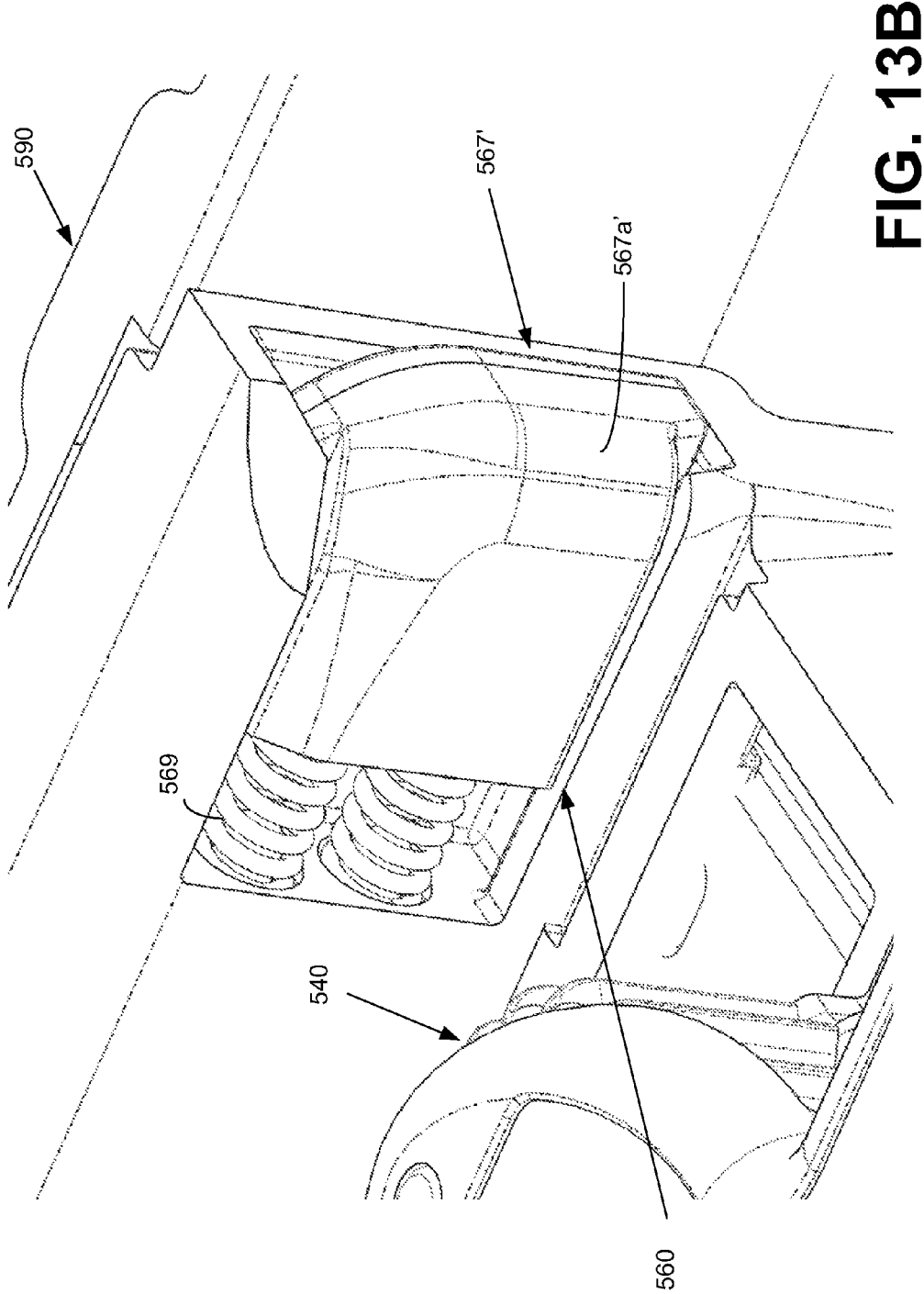

In other embodiments, such as the embodiment illustrated in FIG. 10, the reservoir system 501 may include an housing 590 and a bias member 554, which may be similar to the bias member 553 (e.g., FIG. 9). The housing 590 may be for enclosing at least a portion of the drive member 540 and at least a portion of the plunger arm 526. In various embodiments, the housing 590 may also enclose other drive components or portions thereof, such as, a drive motor (not shown) and/or other drive member(s)/linkage operatively connecting the drive member 540 and the drive motor (not shown). In particular embodiments, the housing 590 may be the durable housing 30 (e.g., FIGS. 1-6C).

With reference to FIGS. 7A-10, in some embodiments, the reservoir system 501 may include a plunger arm casing (not shown) that may have an opening 536 for allowing a portion of the engagement side 528 of the plunger arm 526 to operatively engage the drive member 540. In such embodiments, the plunger arm 526 may be completely surrounded by the plunger arm casing (not shown) and/or the reservoir body 510. Accordingly, only the portion of the engagement side 528 of the plunger arm 526 exposed by the opening 536 may not be covered by the plunger arm casing (not shown) and/or the reservoir body 510, thus allowing the drive member 540 to operatively engage the engagement side 528 of the plunger arm 526. In further embodiments, the plunger arm casing (not shown) may be adapted to allow the bias member 554 to contact the plunger arm 526. For example, the plunger arm casing (not shown) may include a second opening for allowing the bias member 554 to contact the plunger arm 526.

In some embodiments, the housing 590 and/or the plunger arm casing 530 may be configured for minimizing an expansion of the reservoir body 510, for example, as pressure within the reservoir body 510 increases during use. In such embodiments, by fitting the housing 590 to the back of the reservoir body 510 in one or more dimensions, the housing 590 may help to retain a shape of the reservoir body 510.

In various embodiments where the reservoir system 501 is pre-filled with fluidic media, the reservoir 510 may include a plunger head (e.g., 520) that may be attachable to the delivery device (not shown) as described above. In other embodiments, the plunger head may be placed in the reservoir 510 before or after the reservoir 510 is filled with fluidic media.

FIGS. 11-13B illustrate a retention structure 560 that may be employed as an embodiment or employed with a reservoir system (e.g., 501 in FIGS. 7A-10) discussed above for delivering fluidic media in accordance with an embodiment of the present invention. Although the retention structure 560 may be similar or used with the embodiments of FIGS. 7A-10, it should be understood that the retention structure 560 may also include some or all of the same components and operate in a manner similar to that shown and described in the embodiments of FIGS. 1-6C and/or 14-18F. In addition, some or all of the features shown in FIGS. 1-10 and 14-18F may be combined in various ways and included in the embodiments shown in 11-13B. Likewise, it should be understood that any of the features of the embodiments of FIGS. 11-13B may be combined or otherwise incorporated into any of the other embodiments of FIGS. 11-13B as well as any other embodiment herein discussed. Also, the retention structure 560 may be employed or used with other types of delivery device systems and/or components other than those described in the disclosure. In various embodiments, the retention structure 560 may be employed with a medical device 500.

With reference to FIGS. 7A-13B, in some embodiments, the reservoir system 501 may be used with and/or include the retention structure 560 configured to provide a pre-determined force to the reservoir body 510, such that the reservoir body 510 is properly positioned inside the medical device 500 while inserted in the medical device. In various embodiments, the retention structure 560 may be configured to ensure that a position of the reservoir body 510 is maintained during operation of the medical device 500.

In some embodiments, the retention structure 560 may comprise a rigid member 567 that may, for example (but not limited to), have a wedge shape and a bias member 569 arranged to operatively engage the plunger arm casing 530 (and/or the plunger arm 526). For instance, in some embodiments, the reservoir system 501 may include a flange 562 (or other surface) facing the retention structure 560. In some embodiments, for example, the bias member 569 may be similar to the bias member 553, 554 (e.g., FIGS. 9 and 10). The rigid member 567 may be made of any suitably rigid material made of, but not limited to, plastic, composite material, metal, glass, ceramic, or the like.

During insertion of the reservoir body 510, the rigid member 567 may be pushed rearward in Direction D1 by the flange 562 of the reservoir body 510 interacting with an engagement face 567*a* of the rigid member 567. Movement of the rigid member 567 in the Direction D1 may compress the bias member 569, which may cause an increase in a force in Direction D2. The flange 562 may be made of any suitably rigid material made of, but not limited to, plastic, composite material, metal, glass, ceramic, or the like.

In some embodiments, the engagement face 567*a* of the rigid member 567 may be angled (e.g., FIG. 12) so that the rigid member 567 applies a force in a Direction D3, which corresponds to the angle of the engagement face 567*a*. As such, the force in the Direction D3 is split into two components: (a) a force F1 in the Direction D4, which may correspond to the Direction D2, and (b) a force F2 in Direction D5, which may be substantially perpendicular the Direction D4 of the force F1. Throughout various embodiments, a magnitude of each of the forces F1, F2 generated in each respective direction (and/or the Directions D4 and D5) may be determined based on the angle on the engagement face 567*a* of the rigid member 567 (and/or the angle of the flange 562).

Figure 14:
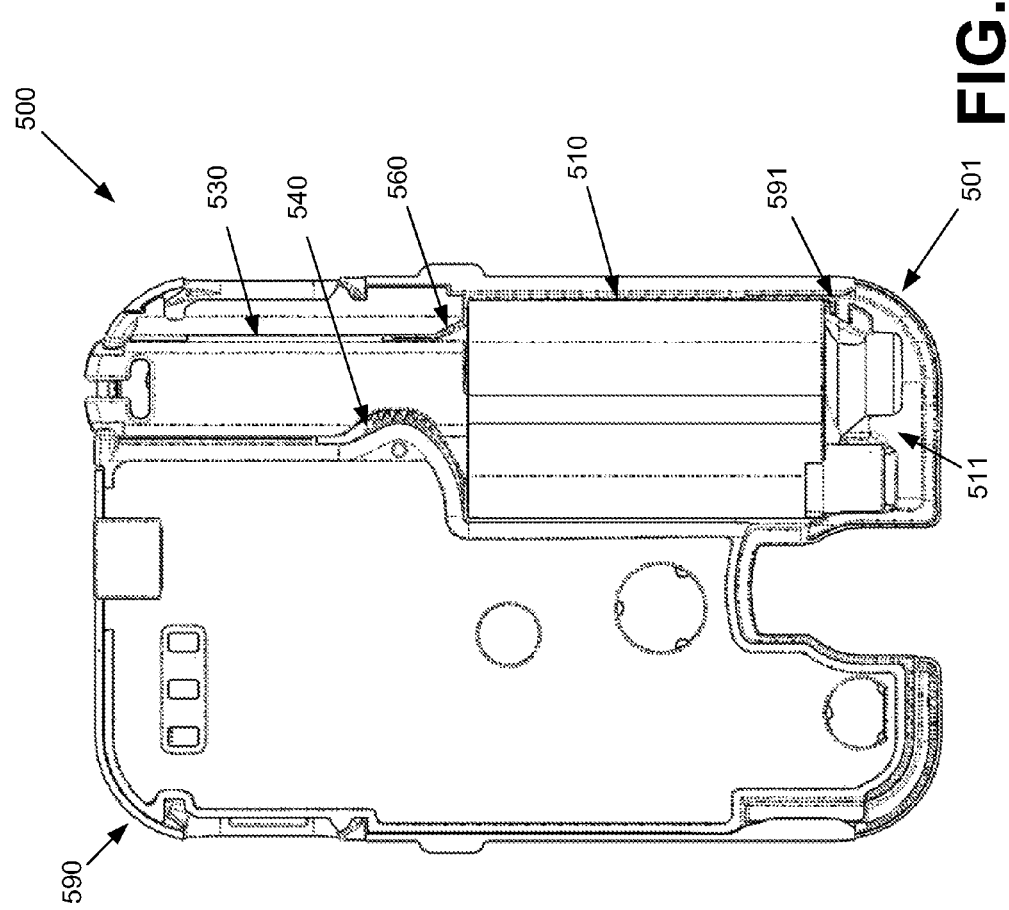
FIG. 14 illustrates a portion of a medical device in accordance with an embodiment of the present invention.
Figure 15:
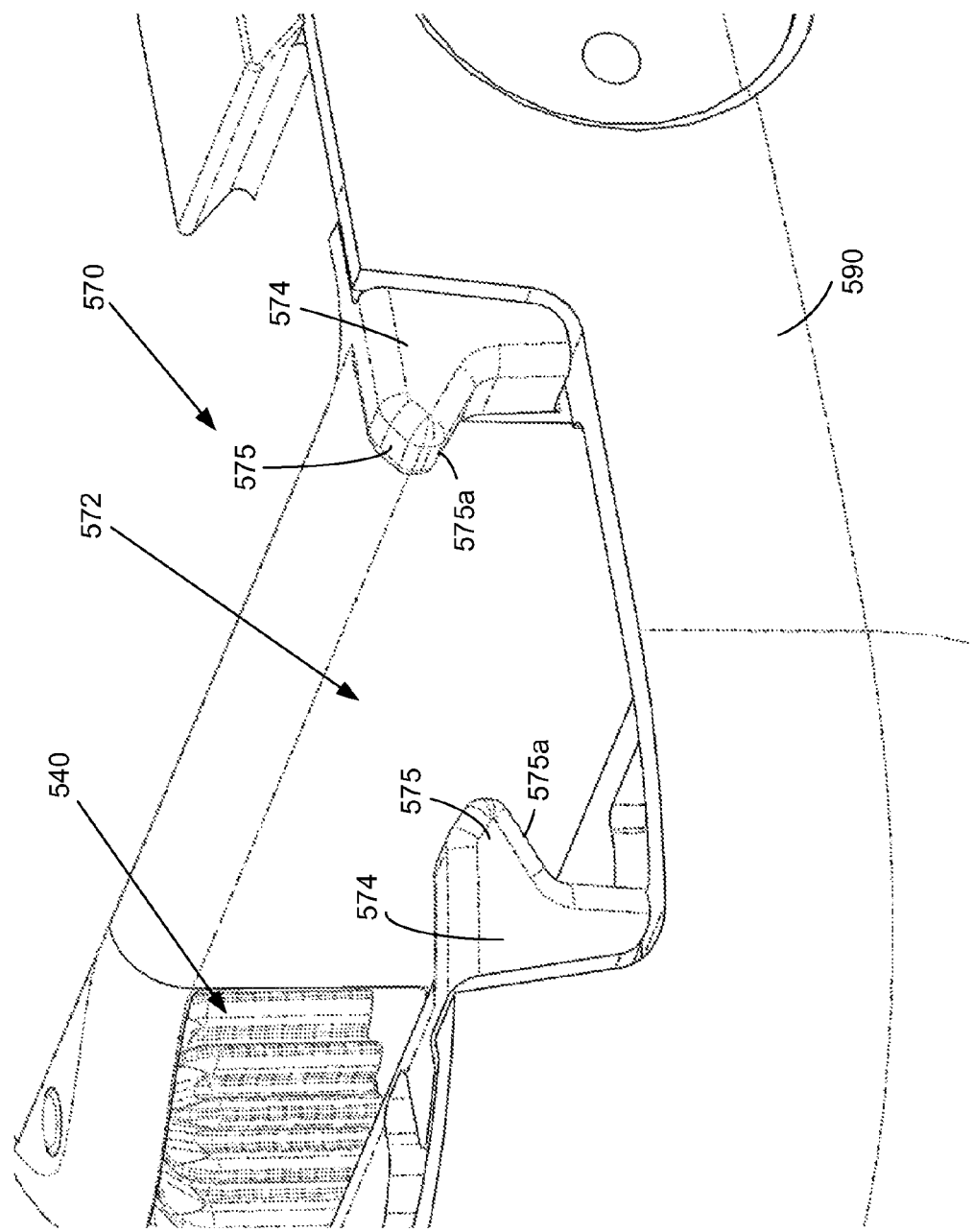
FIG. 15 illustrates a portion of a medical device in accordance with an embodiment of the present invention.
Figure 17:
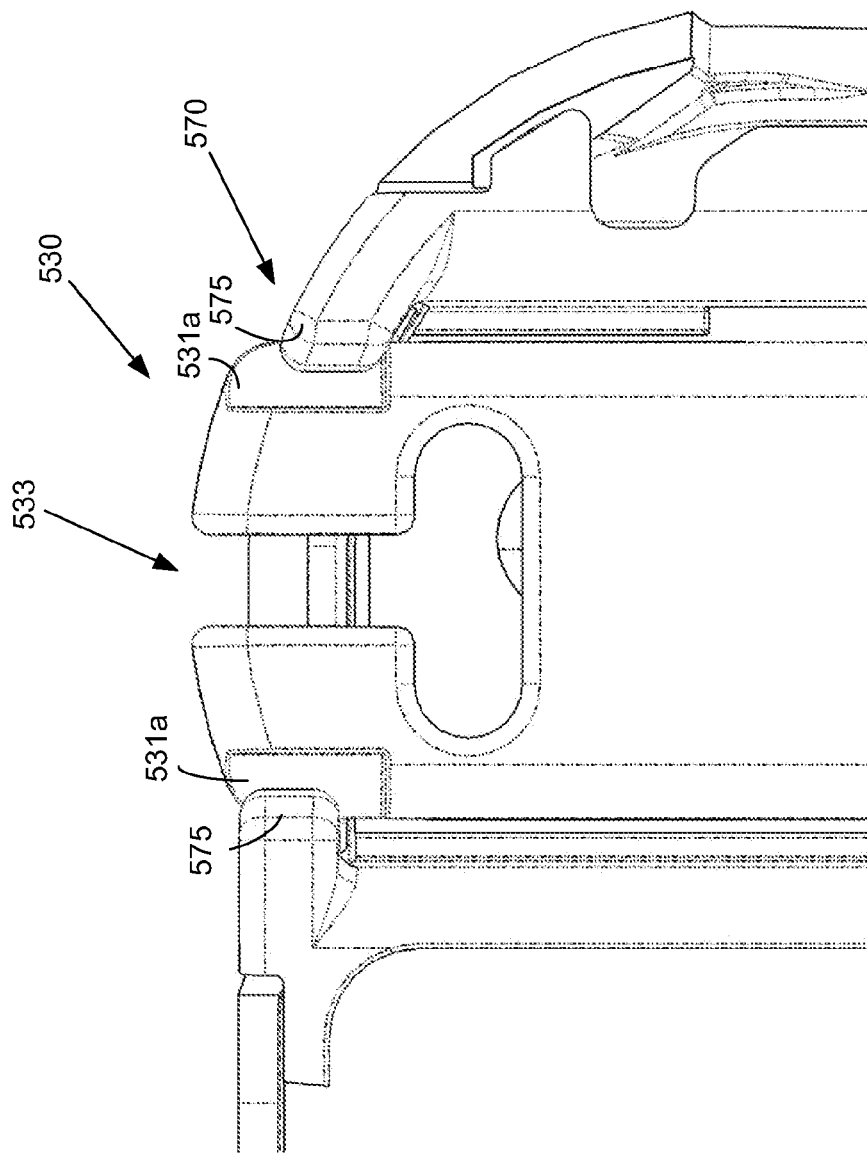
FIG. 17 illustrates a portion of a medical device in accordance with an embodiment of the present invention.
Figure 18D:
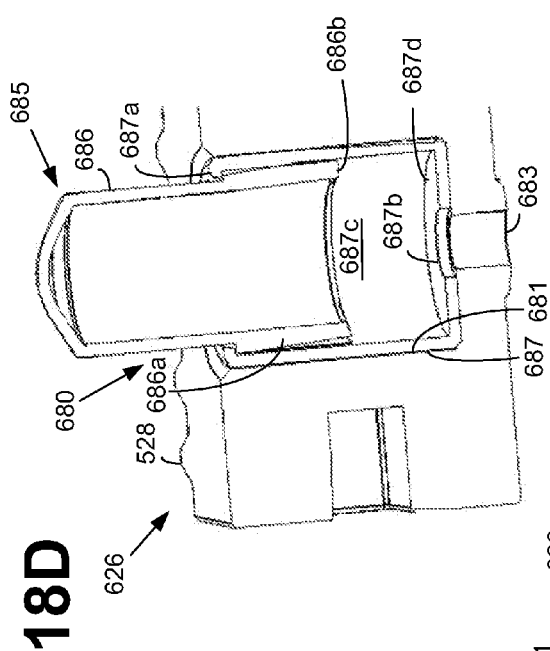
Figure 18F:
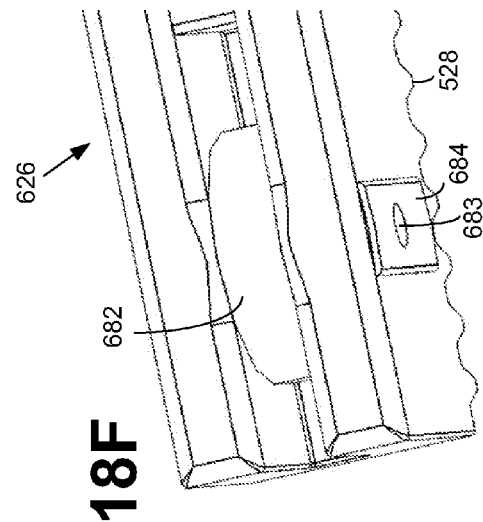
Figure 18E:
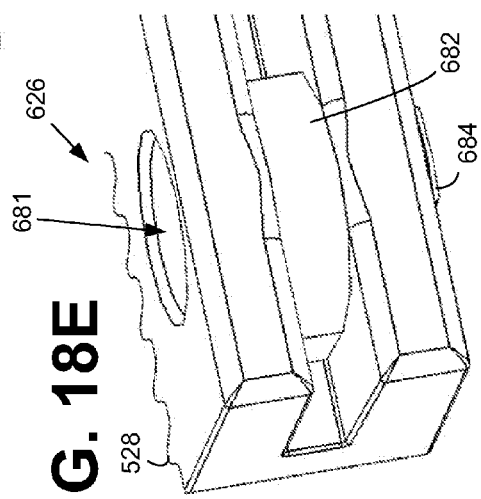

The force F1 generated in the Direction D4 by the rigid member 567 may position a front face 511 of the reservoir body 510 against a predetermined datuming point inside the housing 590, such as (but not limited to) inner face 591 (e.g., FIG. 14). In particular embodiments, the reservoir body 510 may be biased against the inner surface 591 (or other datuming point) with a sufficient force to overcome any forces associated with fluid connection (e.g., engagement of the reservoir with a needle or other fluid conduit, engagement of the reservoir with pierceable members surrounding the needle, portions of the reservoir engaging other components). Examples of fluid connection systems are described in, but not limited to, the patent application Ser. No. 12/974,106, filed concurrently herewith, which is herein incorporated by reference in its entirety. The force F2 generated in the Direction D5 may position the plunger arm 526 within the plunger arm casing 530 against the drive member 540, which may better ensure that the plunger arm 526 and the drive member 540 are in proper engagement.

In various embodiments, the rigid member 567 may be configured to providing a retaining force against any loads generated by the housing 590 (or other portion) upon the reservoir body 510, which could potentially cause the reservoir body 510 to move out of position and/or cause an unintended delivery of fluidic media from the reservoir body 510. In some embodiments, the retention structure 560 may be configured to resist a load or force generated from the drive member 540 (or other component operatively connected to the drive member 540) upon the reservoir body 510, which could potentially cause the reservoir body 510 to move out of position and/or cause an unintended delivery of fluidic media from the reservoir body 510.

In various embodiments, the drive member 540 may have teeth or the like for operatively engaging with angled teeth or the like of the plunger arm 526. In some embodiments, the teeth of the drive member 540 (and/or the teeth of the plunger arm 526 may be angled such that the angled surface is less than 90° relative to the drive member 540 (and/or plunger arm 526, respectively), for example in a triangular or saw tooth pattern. As such, the drive member 540 may apply a force to the reservoir body 510 depending on how the angle of the teeth of the drive member 540 and the plunger arm 526 engage. As a result, in a case where the drive member 540 and the plunger arm 526 are operatively engaged and the drive member 540 is rotated, the plunger arm 526 may be driven in the Direction D4. As previously discussed, movement of the plunger arm 526 in the Direction D4 may cause the plunger arm 526 operatively connected to the plunger arm 526 to move inside the reservoir body 510 in the same direction. Movement of the plunger arm 526 may act (e.g., by creating pressure) upon the fluidic media in the reservoir body 510, forcing the fluidic out of the reservoir body 510. In the described embodiments, for example, the retention structure 560 may retain the reservoir 510 and/or the plunger arm 526 in place by resisting force caused by this buildup of pressure upon the plunger arm 526, which acts in direct opposition to force (in the Direction D4) by the rotating drive member 540, which may force the reservoir body 510 may be forced away from the drive member 540 due to the angled teeth of the plunger arm 526 and drive member 540.

In some embodiments, the retention structure 560 may be configured to resist a load or force generated upon the reservoir body 510 from fluid connection members or components related to such. Examples of fluid connection systems are described in, but not limited to, the patent application Ser. No. 12/974,106, filed concurrently herewith, which is herein incorporated by reference in its entirety. For instance, in some embodiments, the retention structure 560 may be configured to resist a load or force generated upon the reservoir body 510 from a needle or the like as the needle pierces (or otherwise establishes a fluid path with) the reservoir body 510.

As another example, the retention structure 560 may be configured to resist a load or force generated upon the reservoir body 510 from a pierceable member, such as that described in, but not limited to, the patent application Ser. No. 12/974,106, filed concurrently herewith, which is herein incorporated by reference in its entirety. For instance, the pierceable member may include a collapsible member that covers the needle of the fluid delivery path of the first member. When the second member is mounted onto the first member, the pierceable member may collapse over the needle allowing the needle to penetrate the reservoir body 510. Due to the elastomeric nature of the pierceable member, when the pierceable member is compressed, the pierceable member may apply a force (e.g., in the Direction D1) onto the reservoir body 510 (e.g., a front surface of the reservoir body 510). In various embodiments, the retention structure 560 may inhibit the reservoir body 510 to become disconnected from the fluid delivery path by providing a force greater than the force applied by the pierceable member.

In some embodiments, the retention structure 560 may be configured such that force provided by the bias member 569 may be less than the force the rigid member 567 is intended to resist. In particular embodiments, the engagement face 567*a* of the rigid member 567 may be angled such that the engagement surface 567*a* is less than 90° relative to the direction of the bias force (Direction D2). For example, the engagement face of the rigid member 567 may be angled to complement an engagement surface 562a of the flange 562. In such embodiments, the amount of force that needs to be applied to the engagement face 567a of the rigid member 567 to cause the rigid member 567 to shift position may be dependent on one or more of the following factors that may be selected during manufacture, for example, the angle of the engagement face 567a of the rigid member 567, the direction from which the force that is applied to the engagement face 567a is applied, and/or the force generated by the bias member, for example, 569.

In other embodiments, the engagement face 567a of the rigid member 567 and/or the engagement face 562a of the flange 562 may be of any suitable shape for engaging each other. For instance, with reference to FIG. 13B a rigid member 567' may include a round engagement surface 567' or any other suitably-shaped surface. In further embodiments, the engagement face 562a of the flange 562 of the plunger arm casing 530 (e.g., FIG. 13A) may be angled, for example, as described with respect to the engagement surface 567a (e.g., FIG. 13A). In other embodiments, the flange 562 may include a face having any suitable shape, for example (but not limited to) a round engagement surface, for example, as described with respect to the engagement face 562a (e.g., FIG. 13A).

With reference to FIGS. 7A-13B, in various embodiments, the reservoir system 501 may include the flange 562 on which the rigid member 567 acts. In other embodiments, the rigid member 567 may act directly on the plunger arm casing 530 without a flange therebetween.

In various embodiments, the plunger arm casing 530 includes the flange 562. In other embodiments, the plunger arm 526 (or other portion operatively connected to the plunger arm 526) may include the flange 562. Thus, in such embodiments, the rigid member 567 applies a force to the plunger arm 526 via the flange 562. In yet other embodiments, the rigid member 567 may be configured to apply a force directly to the plunger arm 526 without a flange 562 therebetween. In various embodiments, the rigid member 567 may be configured to provide a force upon any suitable element (not shown) arranged between the rigid member 567 and the plunger arm casing 530 (or the plunger arm 526) such that the force on the element causes the element to act on the plunger arm casing 530 (or the plunger arm 526) or other element operatively engaging the element and the plunger arm casing 530 (or the plunger arm 526).

FIGS. 14-17 illustrate a securing structure 570 that may be employed with a reservoir system (e.g., 501 in FIGS. 7A-13B) discussed above for delivering fluidic media in accordance with an embodiment of the present invention. Although the securing structure 570 may be similar or used with the embodiments of FIGS. 7A-13B, it should be understood that the securing structure 570 may also include some or all of the same components and operate in a manner similar to that shown and described in the embodiments of FIGS. 1-6C and/or 18A-18F. In addition, some or all of the features shown in FIGS. 1-13B and 18A-18F may be combined in various ways and included in the embodiments shown in 14-17. Likewise, it should be understood that any of the features of the embodiments of FIGS. 14-17 may be combined or otherwise incorporated into any of the other embodiments of FIGS. 14-17 as well as any other embodiment herein discussed. Also, the securing structure 570 may be employed or used with other types of delivery device systems and/or components other than those described in the disclosure. In various embodiments, the securing structure 570 may be employed with the medical device 500 or the like.

With reference to FIGS. 7A-17, in various embodiments, the housing 590 (or other component) may be configured to receive and secure at least a portion of the reservoir system 501. In particular embodiments, the housing 590 (or other component) may be configured to receive and secure the plunger arm casing 530 (and/or the plunger arm 526).

In some embodiments, the housing 590 may include the securing structure 570. The securing structure 570 may include a receptacle 572 or the like provided in the housing 590. The receptacle 572 may be suitably shaped to receive at least a portion of the reservoir system 501. In particular embodiments, the receptacle 572 may be suitably shaped to receive the reservoir system 501.

The securing structure 570 may include one or more securing members 574 (e.g., a clip member) for securing or otherwise engaging a portion of the reservoir system 501, such as the plunger arm casing 530, in the receptacle 572. The securing members 574 may include tabs 575, protrusions, or the like. In particular embodiments, the securing members 574 and/or the tabs 575 may be configured to receive and secure (or otherwise engage) a portion of the reservoir system 501, such as the plunger arm casing 530, in any suitable manner, including (but not limited to) with a snap-fitting configuration, friction fitting configuration, dovetail fitting configuration, or the like. In particular embodiments, the securing members 574 and/or the tabs 575 may be configured to receive and secure an end 531 of the plunger arm casing 530.

In some embodiments, tabs 575 (and/or the securing members 574) may include angled faces 575a for mating with the at least a portion of the reservoir system 501 (e.g., the plunger arm casing 530). In some embodiments the at least a portion of the reservoir system 501 (e.g., the plunger arm casing 530) may include angled faces 531a for mating with the tabs 575 (and/or the securing members 574). Thus, in some embodiments, the angled faces 575a of the tabs 575 may be for mating with the angles faces 531a of the at least a portion of the reservoir system 501.

In some embodiments, any or each of the securing structure 570, the securing members 574, and the tabs 575 may be integral with the housing 590. In other embodiments, any or each of the securing members 570, the securing members 574, and the tabs 575 may be a separate component connected to the housing 590 in any suitable manner, including (but not limited to), press-fitting, adhesive, friction-fitting, or the like. In various embodiments, any or each of the securing structure 570, the securing members 574, and the tabs 575 may be made of any suitably-rigid material, such as (but not limited to) plastic, composite material, or the like.

In some embodiments, at least a portion of the reservoir system 501 (e.g., the plunger arm casing 530) may be configured to facilitate insertion of the at least a portion and/or increase engagement between the at least a portion and the securing members 574. In particular embodiments, the plunger arm casing 530 (e.g., on the end 531) may include a cut-out or other depression 533, for example, on an upper portion (or other suitable location) of the plunger arm casing 530 to allow the faces 531a to compress to fit between the tabs 575 (i.e., the faces 531a flex toward each other) during insertion of the reservoir system 501 into the securing structure 570.

In various embodiments, the securing structure 570 may hold firmly inside the housing 590 such that, for example, the reservoir system 501 properly engages and actuates a sensor, such as a volume sensor (not shown), occlusion sensor, and/or the like, examples of which are disclosed in (but not limited to), U.S. patent application Ser. No. 12/649,619, filed Dec. 30, 2009, entitled "Alignment Systems and Methods," herein incorporated by reference in its entirety; U.S. Pat. No. 6,485,465, filed Mar. 27, 2001, entitled "Methods, Apparatuses, and Uses for Infusion Pump Fluid Pressure and Force Detection"; U.S. Pat. Pub. No. US 2006/0184154, filed Dec. 30, 2005, entitled "Methods and Apparatuses for Detecting Occlusions in an Ambulatory Infusion Pump"; and U.S. Pat. Pub. No. US 2007/0191770, filed Nov. 20, 2006, entitled "Method and Apparatus for Detecting Occlusions in an Ambulatory Infusion Pump," all of which are herein incorporated by reference.

In various embodiments, the securing structure 570 may align the reservoir system 501 into a pre-defined position of the housing 590 to providing proper alignment of the reservoir system 501 and/or associated components, such as the volume sensor and/or the like.

In various embodiments, the housing 590 may be may be configured to receive and secure the reservoir system 501 (or components thereof). In other embodiments, other components, such as (but not limited to) the first member (e.g., 202) and the second member (e.g., 203) may be configured to receive and secure the reservoir system 501 (or components thereof). In some embodiments, the housing 590 (or other component) may be configured to receive and secure the plunger arm casing 530. In some embodiments, the housing 590 (or other component) may be configured to receive and secure a component operatively connected to the plunger arm casing 530, such as (but not limited to) the plunger arm 526.

In various embodiments, the reservoir system 501 may be configured to actuate a sensor (not shown), such as the volume sensor or other component. For instance, the reservoir system 501 may actuate the volume sensor when the reservoir system 501 (or the at least a portion of the reservoir system 501) is inserted to the housing 590.

FIGS. 18A-18F illustrate an actuation structure 680 that may be employed as an embodiment, or employed with a reservoir system (e.g., 501 in FIGS. 7A-17) discussed above, for delivering fluidic media in accordance with an embodiment of the present invention. Although the actuation structure 680 may be similar or used with the embodiments of FIGS. 7A-17, it should be understood that the actuation structure 680 may also include some or all of the same components and operate in a manner similar to that shown and described in the embodiments of FIGS. 1-6C. In addition, some or all of the features shown in FIGS. 1-17 may be combined in various ways and included in the embodiments shown in 18A-18F. Likewise, it should be understood that any of the features of the embodiments of FIGS. 18A-18F may be combined or otherwise incorporated into any of the other embodiments of FIGS. 18A-18F as well as any other embodiment herein discussed. Also, the actuation structure 680 may be employed or used with other types of delivery device systems and/or components other than those described in the disclosure. In various embodiments, the actuation structure 680 may be employed with the medical device 500 or the like.

With reference to FIGS. 18A-18F, in some embodiments, the reservoir system 501 may include a plunger arm 626, which may be substantially similar to the plunger arm 526. The plunger arm 626 may include the actuation structure 680 for actuating the sensor.

In some embodiments, the actuation structure 680 may include an actuation member 685 arranged in or on the plunger arm 626, for example in a recess 681 provided in the plunger arm 626. In some embodiments, the recess 681 may be formed in the plunger arm 626. In other embodiments, the plunger arm 626 may include a receiving body 682 in which the recess 681 is formed. The actuation member 685 may be secured or otherwise arranged in the recess 681 in any suitable manner, for example (but not limited to), in a friction-fitting configuration, snap-fitting configuration, with an adhesive material, or the like.

In various embodiments, the actuation member 685 may include an assembly having a first member 686 and a second member 687. The second member 687 may be sized and configured to fit and be secured within the recess 681 as described with respect to the actuation member 685 as a whole.

The first member 686 may be arranged at least partially in an interior chamber 687c of the second member 687. The first member 686 may be arranged for movement relative to the second member 687 such that an end of the first member 686 may extend beyond the interior chamber 687c of the second member 687 (in a direction away from the plunger arm 626).

In some embodiments, one or more of the first and second members 686, 687 may be made of a conductive material, such as metal or the like, to establish an electrical connection with the sensor. In other embodiments, one or more of the first and second members 686, 687 may be made of a conductive material, such as metal or the like, to provide a connection between the sensor (e.g., on end of the actuation member 685) and other suitable circuitry (e.g., on an opposite end of the actuation member 685). In other embodiments, the first member 686 and/or the second member 687 need not be made of a conductive material, for example, as described below.

Examples of the circuitry configuration for the sensor are described in, but are not limited to, U.S. application Ser. No. 12/649,619 (filed Dec. 30, 2009), which is herein incorporated by reference in its entirety.

The actuation member 685 may include a bias member (not shown) arranged, for example, in the interior 687c. The bias member, which may be (but is not limited to) a spring or the like, may be arranged to provide a bias force on the first member 686 in the direction away from the plunger arm 626. The bias force may be enough to move (and/or maintain) the first member 686 away from the second member (in the direction away from the plunger arm 626), yet allow the first member 686 to be moved by the sensor or a portion of the housing 590 (or other component) in the opposite direction when the reservoir system 501 (e.g., FIGS. 7A-16B) is inserted, for example, as previously described. In some embodiments, the bias member may be arranged between a bottom surface 686b of the first member 686 and a floor surface 687d (or other surface of the first member 686 facing the floor surface 687d).

The actuation structure 680 may be arranged relative to the sensor such that insertion of the plunger arm 626 allows the first member 686 to actuate the sensor. For instance, in some embodiments, upon insertion of the reservoir system 501, the first member 686 may contact the sensor to establish a connection with the sensor. In other embodiments, upon insertion of the reservoir system 501, the first member 686 may contact the sensor to establish a connection with the sensor, which is fixed or otherwise operatively connected) to the outer housing, such that the sensor moves the first member 686 (against the bias force) toward the second member 687. Continued movement of the first member 686 (e.g., during continued insertion of the reservoir system 501) may establish an electrical connection with suitable circuitry. For instance, the bottom surface 686b (or other portion) may contact suitable circuitry (or electrical conductors to such), which may establish an electrical connection between the sensor and the circuitry.

Because the plunger arm 626 is moveable, the sensor may be arranged and/or configured to extend along at least a portion of the plunger arm 626. Accordingly, the actuation member 685 may contact different portions of the sensor as the plunger arm 626, for example, to deliver (or receive) fluidic media. Each of these portions contacted by the actuation member 685 may correspond to different information (from another portion of the sensor) (e.g., varying volumes of fluidic media in the reservoir).

In other embodiments, a plurality of sensors may be provided along the path of travel of the plunger arm 626. Thus, the sensor of the plurality of sensors that is engaged by the actuation member 685 may correspond to different information (from another sensor of the plurality of sensors). Further examples of such embodiments are disclosed in, but not limited to, U.S. application Ser. No. 12/649,619 (filed Dec. 30, 2009), which is herein incorporated by reference.

For instance, in a case where the sensor is a volume sensor, the volume sensor may be activated upon insertion of the reservoir system 501. Furthermore, a position at which the actuation member 685 contacts the volume sensor may correspond to an amount of fluidic media left in the reservoir 510. As the plunger arm 626 moves forward to deliver fluidic media in the reservoir 510, the actuation member 686 moves along the volume sensor. The new position(s) at which the actuation member 686 contacts the volume sensor may correspond to a current amount of fluidic media in the reservoir. Thus, in various embodiments, the actuation structure may allow for actuation of a sensor (e.g., a volume sensor) and/or may allow for providing position information of the actuation member 686 (and thus other components of or connected to the plunger arm 626), which can allow for sensing a volume in a reservoir.

Further examples of actuation members that allow for providing position information of the actuation member 686 (and thus other components of or connected to the plunger arm 626) are disclosed in, but are not limited to, U.S. application Ser. No. 12/649,619 (filed Dec. 30, 2009), which is herein incorporated by reference.

In various embodiments, the actuation member 685 may actuate an other member that is operatively engageable with the sensor. Further examples of actuation members that operatively engage other components such as a sensor are disclosed in, but not limited to, U.S. application Ser. No. 12/649,619 (filed Dec. 30, 2009), which is herein incorporated by reference. For example, the other member me be a Mylar film or other conductive material upon which the actuation member 685 presses to force a portion of the Mylar film to contact the sensor. In such embodiments, for example, the actuation member 685 need not be made of a conductive material because the electrical connection occurs between the Mylar film and the sensor. Thus, in some embodiments, the other member may be a flexible member or the like. In other embodiments, the other member may be arranged for movement by the actuation member 686 toward the sensor.

In some embodiments, the second member 687 may include a lip portion 687*a* or the like for preventing a base portion 686*a*, which has a wider diameter than a remaining portion of the first member 686, of the first member 686 from leaving the interior 687*c* of the second member 687. In further embodiments, the bias member (or other suitable member for providing a bias or driving force) may be arranged between the lip portion 687*a* or the base portion 686*a*. In other embodiments, the plunger arm 626 may have a lip portion, which may be similar to the lip portion 687*a*, for retaining the actuation member 685 in place. In yet other embodiments, the lip portion of the plunger arm 626 may prevent the base portion 686*a* first member 686 from leaving the interior 687*c* of the second member 686 instead of (or in addition to) the lip portion 687*a* of the second member 687. In some of these embodiments, for example, the bias member may be arranged between the lip portion of the plunger arm 626 and the base portion 686*a* of the first member 686, for example, as previously described With reference to FIGS. 15-18F, in various embodiments, the sensor may be actuated by the actuation member 685. In such embodiments, force that is generated by the actuation member 685 may be used to actuate the sensor. However, the force may also push the reservoir system 501 (or a portion thereof) out of the position. In such a case, the securing members 574 may retain the reservoir system 501 in place.

In particular embodiments, a force required to remove the reservoir system 501 (or a portion thereof) from the securing members 574 may be greater than the force generated by the actuation member 685, otherwise the reservoir system 501 could be displaced. For example, the faces 675*a* on the tabs 675 and/or overlap between the securing members 674 and the reservoir system 501 may be adapted or otherwise configured such that the force to remove the reservoir system 501 from the securing members 674 is greater than the force generated by the actuation member 685, but not so great as to make it difficult to remove the reservoir system from the securing members 674 by the user.

With reference to FIGS. 7A-18F, in various embodiments, the housing 590 may be configured to include a bulge area adjacent an area where the reservoir body 510 is positioned. The bulge area may be a convex portion on the exterior surface of the housing 590. The reservoir body 510 may be positioned on the opposite side of the housing 590 (e.g., within the housing 590). In such embodiments, a force applied to the bulge area may compress the bulge area toward the reservoir body 510 while minimizing or preventing the bulge area from pressing upon the reservoir body 510. As such, the bulge area may help inhibit fluid from being expelled from the reservoir body 510, pressure from increasing within the reservoir body 510, moving the reservoir body 510 (and/or the reservoir system 501) from out of proper position, a force from being applied on the drive device, and/or the like. For example, a user or the like could squeeze or otherwise press (intentional or otherwise) the bulge area of the housing 590 without adversely affecting the reservoir system 501.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A system for retaining a fluid delivery device in a housing, the fluid delivery device comprising a reservoir, the system comprising:

a plunger arm operatively connected to a plunger head arranged for movement in an axial direction within the reservoir, the plunger arm having an arm portion operatively engageable with a drive member configured to move the plunger arm and the plunger head in the axial direction when the plunger arm and the plunger head are connected to the drive member;

a casing arranged between the plunger arm and the drive member, the casing configured to support the plunger arm and to envelop at least a portion of the plunger arm, the casing having an opening for allowing the arm portion of the plunger arm to operatively engage the drive member;
a rigid member arranged for movement; and
a bias member configured to move the rigid member to bias the plunger arm in a first direction against the drive member to operatively engage the drive member for movement by the drive member in the axial direction;
wherein the first direction is transverse to the axial direction.

2. The system of claim 1, the bias member configured to urge the rigid member toward the casing to cause the casing to force the plunger arm against the drive member.

3. The system of claim 1, wherein the bias member comprises a spring.

4. The system of claim 1, wherein the bias member is configured to move the rigid member toward the plunger arm to move the plunger arm in the first direction toward the drive member to operatively engage the plunger arm to the drive member.

5. The system of claim 1,
wherein the bias member is configured to prevent the plunger arm from moving in a second direction away from the drive member;
wherein the second direction is opposite the first direction and is transverse to the axial direction.

6. A system for retaining a fluid delivery device in a housing, the fluid delivery device comprising a reservoir and a plunger arm operatively connected to a plunger head arranged for movement in an axial direction within the reservoir, the plunger arm having an arm portion operatively engageable with a drive member configured to move the plunger arm and the plunger head in the axial direction when the plunger arm and the plunger head are connected to the drive member, the system comprising:
a rigid member arranged for movement; and
a bias member configured to move the rigid member to bias the plunger arm in a first direction against the drive member to operatively engage the drive member for movement by the drive member in the axial direction;
wherein the first direction is transverse to the axial direction; and
wherein the bias member is further configured to urge the rigid member such that the rigid member provides a force against the casing in a first direction to cause the casing to urge the plunger arm against the drive member, and in a second direction to urge the casing against a surface of the housing, the second direction being transverse to the first direction.

7. The system of claim 6, further comprising:
the plunger arm; and
a casing arranged between the plunger arm and the drive member, the casing configured to support the plunger arm and to envelop at least a portion of the plunger arm.

8. The system of claim 7, the casing having an opening for allowing the arm portion of the plunger arm to operatively engage the drive member.

9. The system of claim 7, the housing configured to support the drive member, the plunger arm, the rigid member, and the bias member.

10. The system of claim 6, wherein the first direction is substantially perpendicular to the second direction.

11. The system of claim 6, wherein the second direction is substantially parallel to a direction in which the rigid member is urged.

12. The system of claim 6,
the rigid member having a contact surface for engaging the casing;
wherein the contact surface is substantially round.

13. The system of claim 6, wherein the rigid member comprises a wedge-shaped member.

14. A system for retaining a fluid delivery device in a housing, the fluid delivery device comprising a reservoir, the system comprising:
a plunger arm operatively connected to a plunger head arranged for movement in an axial direction within the reservoir, the plunger arm having an arm portion operatively engageable with a drive member configured to move the plunger arm and the plunger head in the axial direction when the plunger arm and the plunger head are connected to the drive member;
a casing arranged between the plunger arm and the drive member, the casing configured to support the plunger arm and to envelop at least a portion of the plunger arm,
a rigid member arranged for movement; and
a bias member configured to move the rigid member to bias the plunger arm in a first direction against the drive member to operatively engage the drive member for movement by the drive member in the axial direction;
wherein the first direction is transverse to the axial direction;
wherein the rigid member has a contact surface for engaging the casing; and
wherein the contact surface is substantially flat.

15. The system of claim 14,
the casing having a contact surface for engaging the contact surface of the rigid member;
wherein the contact surface of the casing corresponds in shape with the contact surface of the rigid member.

16. The system of claim 14, wherein the contact surface of the rigid member is an angled surface of less than 90 degrees relative to a direction in which the rigid member is urged.

17. A method of manufacturing a system for retaining a fluid delivery device in a housing, the fluid delivery device comprising a reservoir, the method comprising:
connecting a plunger arm to a plunger head arranged for movement in an axial direction within the reservoir, the plunger arm having an arm portion operatively engageable with a drive member configured to move the plunger arm and the plunger head in the axial direction when the plunger arm and the plunger head are connected to the drive member;
arranging a casing between the plunger arm and the drive member, the casing configured to support the plunger arm and to envelop at least a portion of the plunger arm, the casing having an opening for allowing the arm portion of the plunger arm to operatively engage the drive member;
arranging a rigid member for movement; and
configuring a bias member to move the rigid member to bias the plunger arm in a first direction against the drive member to operatively engage the drive member for movement by the drive member in the axial direction;
wherein the first direction is transverse to the axial direction.

18. A system for retaining a fluid delivery device, the fluid delivery device comprising a reservoir and a plunger arm operatively connectable to a plunger head that is moveable within the reservoir, the plunger arm having an arm portion that is configured for operative engagement to a drive member configured to move the arm portion and the plunger head when the arm portion of the plunger arm is operatively engaged to the drive, the system comprising:

a housing configured to support the plunger arm and the reservoir, the housing having a recess for receiving the plunger arm;

the housing having a pair of protrusions arranged around the recess, the protrusions separated by a gap though which the plunger arm is received into the recess;

the protrusions configured to allow the plunger arm to be forced between the protrusions and received into the recess from a position outside of the recess when a first amount of force is applied on the plunger arm toward the recess;

the protrusions configured to prevent the plunger arm from being removed from the recess using the first amount of force when the plunger arm is in the recess;

the protrusions configured to allow the plunger arm to be removed from the recess through the gap between the protrusions to a position outside of the recess when a second amount of force is applied on the plunger arm away from the recess, the second amount of force being greater than the first amount of force.

19. The system of claim 18, wherein each protrusion has an upper surface that is angled in toward the recess to facilitate insertion of the plunger arm into the recess.

20. The system of claim 18, the system further comprising:
the plunger arm;
wherein the plunger arm has a surface having an angle of less than 90° relative to an upper surface of the plunger arm for engaging each protrusion to facilitate insertion of the plunger arm between the protrusions into the recess.

21. The system of claim 18, the system further comprising:
the plunger arm;
wherein the plunger arm is configured to compress to fit between the protrusions as the plunger arm is inserted between the protrusions into the recess.

22. The system of claim 21, wherein the plunger arm includes an opening that allows the plunger arm to compress to fit between the protrusions as the plunger arm is inserted between the protrusions into the recess.

23. The system of claim 21,
wherein the plunger arm is made of a first material; and
wherein the protrusions are made of a second material that is more rigid than the first material.

24. The system of claim 18, the system further comprising:
the plunger arm, the plunger arm having a width dimension transverse to a direction in which the plunger arm moves;
the gap having a width dimension less than the width dimension of the plunger arm.

25. The system of claim 18, the system further comprising:
the plunger arm;
a plunger arm casing configured to support the plunger arm and to envelop at least a portion of the plunger arm.

26. The system of claim 25, wherein the plunger arm casing has a surface having an angle of less than 90° relative to an upper surface of the plunger arm casing for engaging each protrusion to facilitate insertion of the plunger arm casing between the protrusions into the recess.

27. The system of claim 25, wherein the plunger arm casing is configured to compress to fit between the protrusions as the plunger arm casing is inserted between the protrusions into the recess.

28. The system of claim 27, wherein the plunger arm casing includes an opening that allows the plunger arm casing to compress to fit between the protrusions as the plunger arm casing is inserted between the protrusions into the recess.

29. The system of claim 27,
wherein the plunger arm casing is made of a first material; and
wherein the protrusions are made of a second material that is more rigid than the first material.

30. The system of claim 25, the system further comprising:
the plunger arm casing, the plunger arm having a width dimension transverse to a direction in which the plunger arm moves;
the gap having a width dimension less than the width dimension of the plunger arm casing.

31. The system of claim 18, wherein the gap is in communication with the recess.

32. The system of claim 18, wherein the protrusions define the gap and at least a portion of the recess.

33. The system of claim 18, wherein each of the protrusions extends into the recess.

34. A method of manufacturing a system for retaining a fluid delivery device, the fluid delivery device comprising a reservoir and a plunger arm operatively connectable to a plunger head that is moveable within the reservoir, the plunger arm having an arm portion that is configured for operative engagement to a drive member configured to move the arm portion and the plunger head when the arm portion of the plunger arm is operatively engaged to the drive, the method comprising:
configuring a housing to support the plunger arm and the reservoir, the housing having a recess for receiving the plunger arm; and
arranging in the housing a pair of protrusions around the recess, the protrusions separated by a gap through which the plunger arm is received into the recess;
the protrusions configured to allow the plunger arm to be forced between the protrusions and received into the recess from a position outside of the recess when a first amount of force is applied on the plunger arm toward the recess;
the protrusions configured to prevent the plunger arm from being removed from the recess using the first amount of force when the plunger arm is in the recess;
the protrusions configured to allow the plunger arm to be removed from the recess through the gap between the protrusions to a position outside of the recess when a second amount of force is applied on the plunger arm away from the recess, the second amount of force being greater than the first amount of force.

35. A delivery system for delivering fluidic media to a user, the delivery system comprising:
a first housing portion adapted to be carried by a user;
a second housing portion configured to be selectively operatively engaged with and disengaged from the first housing portion, one of the first housing portion and the second housing portion supporting a reservoir having an interior volume for containing fluidic media and a plunger head moveable within the interior volume of the reservoir along an axial direction of the reservoir, the plunger head operatively connected to a plunger arm;
a drive device supported by the other of the first housing portion and the second housing portion relative to the one of the first housing portion and the second housing portion supporting the reservoir such that upon the first housing portion and the second housing portion being operatively engaged, the reservoir is operatively coupled to the drive device to allow the drive device to move the plunger head via the plunger arm within the interior volume of the reservoir;
a pair of interactive elements including a first interactive element supported on the first housing portion and a second interactive element supported on the second housing portion at a location to be interactable with the first interactive element, the first interactive element comprising a protruding member arranged for movement by the drive device along with the plunger arm and the plunger head, the protruding member for interacting with the second interactive element in a case where the first housing portion and the second housing portion are operatively engaged; and electronic circuitry configured to provide a signal or a change in state in response to the protruding member interacting with the second interactive element when the first housing portion and the second housing portion are operatively engaged.

36. The system of claim 35, wherein the first interactive element comprises a bias member configured to impart a bias force to bias at least one of the protruding member and the second interactive element toward each other.

37. The system of claim 36,
wherein the first interactive element further comprises a housing containing the bias member and at least a portion of the protruding member; and
wherein the housing is fit into the plunger arm.

38. The system of claim 36,
the bias member configured to cause the protruding member to impart the bias force on the second interactive element; and
the circuitry configured to provide the signal or the change in state based on the bias force imparted on the second interactive element.

39. The system of claim 36,
the second housing portion having a recess in which the plunger arm is received;
the second housing portion having a securing structure configured to prevent the plunger arm from being removed from the recess unless a removal force in a direction away from the recess is greater than a minimum threshold;
wherein the bias force imported by the bias member is less than the minimum threshold.

40. The system of claim 35, wherein a position of the protruding member relative to the second interactive element corresponds to reservoir data.

41. The system of claim 40, wherein the reservoir data corresponds to a volume of fluidic media in the reservoir.

42. The system of claim 35, wherein the second interactive element is a sensor.

43. The system of claim 42, wherein the sensor is a volume sensor.

44. The system of claim 43, wherein a position of the protruding member relative to the volume sensor corresponds to reservoir data.

45. The system of claim 44, wherein the reservoir data corresponds to a volume of fluidic media in the reservoir.

46. The system of claim 42, wherein at least one of the first interactive element and the second interactive element comprise a linear sensor.

47. The system of claim 42, the electronic circuitry configured to activate the sensor in response to the protruding member interacting with the second interactive element where the first housing portion and the second housing portion are operatively engaged.

48. The system of claim 35, wherein the protruding member is supported on the plunger arm for movement with the plunger arm.

49. The system of claim 35,
the second interactive element comprising a flexible conductive membrane, the protruding member configured to press against the flexible conductive membrane when the first housing portion and the second housing portion are operatively engaged; and
the electronic circuitry configured to provide the signal or the change in state in response to the protruding member pressing against the flexible conductive membrane.

50. The system of claim 35, the electronic circuitry configured to provide the signal or the change in state in response to the protruding member moving relative to the second interactive element.

51. The system of claim 35, wherein a position of the protruding member relative to the second interactive element corresponds to a remaining quantity of fluidic media in the reservoir.

52. The system of claim 51, wherein the remaining quantity includes at least some fluidic media.

53. The system of claim 35,
wherein a first position of the first interactive element relative to the second interactive element corresponds to a first quantity of fluidic media in the reservoir;
wherein a second position of the first interactive element relative to the second interactive element corresponds to a second quantity of fluidic media in the reservoir; and
wherein the first position is different from the second position, and the first quantity is different from the second quantity.

54. The system of claim 53, wherein the first interactive element continuously interacts with the second interactive element as the first interactive element is moved from the first position to the second position.

55. The system of claim 35, the second interactive element comprising a plurality of interactive elements, the protruding member for interacting with one or more of the interactive elements as the protruding member is moved.

56. The system of claim 35, wherein the protruding member is arranged for movement in a linear direction as the protruding member interacts with the second interactive element.

57. A method of manufacturing a delivery system for delivering fluidic media to a user, the method comprising:
adapting a first housing portion to be carried by a user;
configuring a second housing portion to be selectively operatively engaged with and disengaged from the first housing portion, one of the first housing portion and the second housing portion supporting a reservoir having an interior volume for containing fluidic media and a plunger head moveable within the interior volume of the reservoir along an axial direction of the reservoir, the plunger head operatively connected to a plunger arm;
supporting a drive device by the other of the first housing portion and the second housing portion relative to the one of the first housing portion and the second housing portion supporting the reservoir such that upon the first housing portion and the second housing portion being operatively engaged, the reservoir is operatively coupled to the drive device to allow the drive device to move the plunger head via the plunger arm within the interior volume of the reservoir;
supporting a pair of interactive elements including a first interactive element supported on the first housing portion and a second interactive element supported on the second housing portion at a location to be interactable with the first interactive element, the first interactive element comprising a protruding member arranged for movement by the drive device along with the plunger arm and the plunger head, the protruding member for interacting with the second interactive element in a case where the first housing portion and the second housing portion are operatively engaged; and configuring electronic circuitry to provide a signal or a change in state in response to the protruding member interacting with the second interactive element when the first housing portion and the second housing portion are operatively engaged.

\* \* \* \* \*